US012751634B2

(12) United States Patent
Zheng et al.

(10) Patent No.: US 12,751,634 B2
(45) Date of Patent: Oct. 6, 2026

(54) BLOOD PRESSURE DETECTION METHOD AND APPARATUS

(71) Applicant: Huawei Technologies Co., Ltd., Shenzhen (CN)

(72) Inventors: Chenggong Zheng, Shenzhen (CN); Shaojian Wang, Shenzhen (CN); Zhenlong Huang, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 852 days.

(21) Appl. No.: 17/919,214

(22) PCT Filed: Mar. 23, 2021

(86) PCT No.: PCT/CN2021/082381

§ 371 (c)(1),
(2) Date: Oct. 14, 2022

(87) PCT Pub. No.: WO2021/208679

PCT Pub. Date: Oct. 21, 2021

(65) Prior Publication Data

US 2023/0157553 A1 May 25, 2023

(30) Foreign Application Priority Data

Apr. 16, 2020 (CN) ......................... 202010301533.9

(51) Int. Cl.
*A61B 5/021* (2006.01)
*A61B 5/00* (2006.01)
(Continued)

(52) U.S. Cl.
CPC ...... *A61B 5/02108* (2013.01); *A61B 5/02233* (2013.01); *A61B 5/0531* (2013.01);
(Continued)

(58) Field of Classification Search
CPC ............ A61B 5/02108; A61B 5/02233; A61B 5/0531; A61B 5/1072; A61B 5/1075; A61B 5/681; A61B 5/743; A61B 8/0858; A61B 5/6802; A61B 5/6803; A61B 5/6804; A61B 5/6806; A61B 5/6807; A61B 5/0205; A61B 5/02141; A61B 5/0225; A61B 5/02438;
(Continued)

(56) References Cited

U.S. PATENT DOCUMENTS

2003/0149369 A1* 8/2003 Gallant .................. A61B 5/021 600/485
2010/0036265 A1 2/2010 Kim et al.
(Continued)

FOREIGN PATENT DOCUMENTS

CN 1627916 A 6/2005
CN 205285120 U 6/2016
(Continued)

*Primary Examiner* — Adam J Eiseman
*Assistant Examiner* — Lucy Eppert
(74) *Attorney, Agent, or Firm* — Slater Matsil, LLP

(57) ABSTRACT

A blood pressure detection method is provided. The method comprising: obtaining wrist circumference data, wrist fat thickness data, and blood pressure data and correcting the blood pressure data based on the wrist circumference data and the wrist fat thickness data.

20 Claims, 16 Drawing Sheets

(51) Int. Cl.

| | |
|---|---|
| ***A61B 5/022*** | (2006.01) |
| ***A61B 5/0531*** | (2021.01) |
| ***A61B 5/107*** | (2006.01) |
| ***A61B 8/08*** | (2006.01) |
| ***G16H 50/20*** | (2018.01) |

(52) U.S. Cl.
CPC .......... *A61B 5/1072* (2013.01); *A61B 5/1075* (2013.01); *A61B 5/681* (2013.01); *A61B 5/743* (2013.01); *A61B 8/0858* (2013.01); *G16H 50/20* (2018.01)

(58) Field of Classification Search
CPC ..... A61B 5/0537; A61B 5/4872; A61B 5/742; A61B 5/746; A61B 5/0062; A61B 8/4227; A61B 8/4416; A61B 5/7221; G16H 50/20
See application file for complete search history.

(56) References Cited

U.S. PATENT DOCUMENTS

| | | | | |
|---|---|---|---|---|
| 2010/0105995 | A1* | 4/2010 | Ide | A61B 5/0059 600/310 |
| 2014/0135592 | A1* | 5/2014 | Ohnemus | A61B 5/4266 600/595 |
| 2016/0038055 | A1 | 2/2016 | Wheeler et al. | |
| 2017/0105652 | A1* | 4/2017 | Nebuya | A61B 5/0537 |
| 2018/0168294 | A1* | 6/2018 | Pandolfino | A44C 15/005 |
| 2019/0290143 | A1* | 9/2019 | Iwata | A61B 5/02233 |
| 2019/0365259 | A1 | 12/2019 | Nishikawa et al. | |
| 2021/0093030 | A1* | 4/2021 | Daniel | A41F 9/025 |

FOREIGN PATENT DOCUMENTS

| | | | |
|---|---|---|---|
| CN | 107174245 | A | 9/2017 |
| CN | 207152582 | U | 3/2018 |
| CN | 108402567 | A | 8/2018 |
| CN | 110198661 | A | 9/2019 |
| CN | 212574862 | U | 2/2021 |
| JP | 2002159457 | A | 6/2002 |

* cited by examiner

BLOOD PRESSURE DETECTION METHOD AND APPARATUS

CROSS-REFERENCE TO RELATED APPLICATIONS

This application is a National Stage of International Application No. PCT/CN2021/082381, filed on Mar. 23, 2021, which claims priority to Chinese Patent Application No. 202010301533.9, filed on Apr. 16, 2020, both of which are hereby incorporated by reference in their entireties.

TECHNICAL FIELD

This application pertains to the field of medical instruments, and in particular, to a blood pressure detection method and apparatus.

BACKGROUND

Currently, a mainstream home electronic sphygmomanometer on the market is a wrist electronic sphygmomanometer. For ease of carrying, the wrist electronic sphygmomanometer further evolves into a blood pressure wrist strap, a wrist sphygmomanometer, or a blood pressure watch, to implement blood pressure tracking and monitoring.

When measuring blood pressure at a wrist, the wrist electronic sphygmomanometer measures an air pressure signal in an airbag by using an air pressure sensor connected to the airbag. Ideally, air pressure in the airbag may be delivered to a radial artery without loss through the airbag and a wrist tissue. Therefore, a pulse wave signal can be accurately obtained based on the air pressure signal. However, an actual case is affected by a plurality of factors. For example, in a case of the same wrist circumference, if a subject has relatively thick wrist fat and a radial artery is deeply hidden, because an elastic adipose tissue provides a buffer function, the air pressure in the airbag is greater than pressure actually imposed on the radial artery, and a pulse wave signal moves rightward. Consequently, measured blood pressure is higher than actual systolic blood pressure.

Therefore, for the blood pressure wrist strap, the wrist sphygmomanometer, or the blood pressure watch, when a width and a length of the airbag are fixed, a wrist circumference size and a wrist fat thickness greatly affect the pulse wave signal, causing low accuracy of blood pressure measurement.

SUMMARY

Embodiments of this application provide a blood pressure detection method and apparatus, to improve accuracy of blood pressure measurement.

According to a first aspect, an embodiment of this application provides a blood pressure detection method, including: A wearable device first obtains wrist circumference data, wrist fat thickness data, and blood pressure data. Then, the wearable device corrects the blood pressure data based on the wrist circumference data and the wrist fat thickness data.

The wearable device corrects the blood pressure data based on the wrist circumference data and the wrist fat thickness data, to avoid an impact of a wrist circumference size and a wrist fat thickness on a pulse wave signal, thereby improving accuracy of blood pressure measurement. In addition, the same airbag can be adapted to different people with different wrist circumferences and different wrist fat thicknesses. Target blood pressure can be accurately detected for different users without replacing different types of airbags, to improve compatibility of a blood pressure measurement apparatus and enhance user wearing experience.

In a possible implementation of the first aspect, the blood pressure data may be corrected based on a mapping relationship. The mapping relationship may be a linear fitting function.

For example, the blood pressure data is corrected by using the linear fitting function, and then the corrected blood pressure data is displayed.

It should be understood that the linear fitting function is merely an optional implementation. A possible implementation of the first aspect includes a nonlinear fitting function, for example, a polynomial fitting function.

With reference to the first aspect, in an implementation of the first aspect, obtaining the wrist circumference data includes:

first, detecting an electrical parameter of an adjustable component around the wrist of the user, where the adjustable component includes at least one of an adjustable resistor, an adjustable capacitor, or an adjustable inductor; and then obtaining the wrist circumference data corresponding to the electrical parameter.

Because the wrist circumference data is detected based on the electrical parameter of the adjustable component around the wrist of the user, portability for detection of the wrist circumference data is improved, and the costs of the wrist circumference data are reduced.

With reference to the first aspect, in an implementation of the first aspect, obtaining the wrist fat thickness data includes:

performing impedance detection on the wrist of the user to obtain the wrist fat thickness data; or performing ultrasonic distance detection on the wrist of the user to obtain the wrist fat thickness data.

Because the wrist fat thickness data can be obtained through the impedance detection performed on the wrist of the user, or the wrist fat thickness data can be obtained through the ultrasonic distance detection performed on the wrist of the user, a non-traumatic wrist fat thickness data detection manner is provided, and accuracy of the wrist fat thickness data is improved.

With reference to the first aspect, in an implementation of the first aspect, before obtaining a wrist circumference coefficient, the method further includes:

first, obtaining wrist circumference data, wrist fat thickness data, original blood pressure data, and standard blood pressure data of different figures of people; then performing fitting on the wrist circumference data, the wrist fat thickness data, the original blood pressure data, and the standard blood pressure data of each figure of people to obtain a corresponding mapping relationship; and storing, in a database, the wrist circumference data, the wrist fat thickness data, and the corresponding mapping relationship of each figure of people.

The wrist circumference data, the wrist fat thickness data, the original blood pressure data, and the standard blood pressure data of different figures of people are detected, to expand a range of people to which the mapping relationship is applied, thereby ensuring accuracy of the mapping relationship.

With reference to the first aspect, in an implementation of the first aspect, after the wearable device corrects the blood pressure data based on the wrist circumference data and the wrist fat thickness data, the method further includes:

The wearable device first determines a health level of the user based on the wrist fat thickness data and the detected blood pressure data; and then the wearable device displays the health level.

Because the health level is obtained based on the wrist fat thickness data and the detected blood pressure data, an indicator of the health of the user is comprehensively considered, and accuracy of the health level is improved.

With reference to the first aspect, in an implementation of the first aspect, after the health level of the user is determined, the method further includes:

The wearable device obtains a total calorie intake of the user within unit time; the wearable device obtains total calorie consumption of the user within the unit time; and finally, the wearable device outputs health prompt information based on the total calorie intake, the total calorie consumption, and the health level.

Because the health level is considered when the health prompt information is pushed, the health prompt information is more specific, and the user can obtain the health prompt information matching the personal health level.

With reference to the first aspect, in an implementation of the first aspect, that the wearable device corrects the blood pressure data based on the wrist circumference data and the wrist fat thickness data includes:

First, when the wearable device determines, based on the wrist circumference data and the wrist fat thickness data, that the blood pressure data needs to be corrected, the wearable device obtains, from a preset database, a mapping relationship corresponding to the wrist circumference data and the wrist fat thickness data. The mapping relationship is the mapping relationship corresponding to the wrist circumference data and the wrist fat thickness data. The wearable device corrects the blood pressure data based on the mapping relationship, and displays corrected blood pressure data.

The wearable device obtains, from the preset database, the mapping relationship corresponding to the wrist circumference data and the wrist fat thickness data; and then corrects the blood pressure data based on the mapping relationship, and uses the corrected blood pressure data as the detected blood pressure data. Because the mapping relationship corresponds to the wrist circumference data and the wrist fat thickness data, the blood pressure data is corrected based on the mapping relationship, to further improve accuracy of blood pressure measurement, improve compatibility of a blood pressure measurement apparatus, and enhance user wearing experience.

According to a second aspect, an embodiment of this application provides a blood pressure detection apparatus, including:

a wrist circumference detection component, a wrist fat thickness detection component, a blood pressure detection component, and a processor, where the processor is separately connected to the wrist circumference detection component, the wrist fat thickness detection component, and the blood pressure detection component.

The wrist circumference detection component is configured to obtain wrist circumference data of a user.

The wrist fat thickness detection component is configured to obtain wrist fat thickness data of the user.

The blood pressure detection component is configured to obtain blood pressure data of the user.

The processor is configured to correct the blood pressure data based on the wrist circumference data and the wrist fat thickness data.

The processor corrects the blood pressure data based on the wrist circumference data and the wrist fat thickness data, to avoid an impact of a wrist circumference size and a wrist fat thickness on blood pressure measurement, thereby improving accuracy of blood pressure measurement. In addition, a same airbag can be adapted to different people with different wrist circumferences and different wrist fat thicknesses. Target blood pressure can be accurately detected for different users without replacing different types of airbags, to improve compatibility of the blood pressure measurement apparatus and enhance user wearing experience.

With reference to the second aspect, in an implementation of the second aspect, the blood pressure detection apparatus includes:

a main body part and a strap connected to the main body part, where the strap is configured to wear the main body part on a wrist of the user, and the processor is disposed in the main body part.

The processor is disposed in the main body part, to improve reliability of the blood pressure detection apparatus.

With reference to a third aspect, in an implementation of the third aspect, the wrist circumference detection component includes:

an adjustable component and an electrical parameter detection circuit, where the adjustable component is connected to the electrical parameter detection circuit, and the electrical parameter detection circuit is disposed in the main body part and is configured to: detect an electrical parameter of the adjustable component, and obtain, based on a preset correspondence between the electrical parameter and the wrist circumference data, wrist circumference data corresponding to the detected electrical parameter.

The wrist circumference data is detected by using the adjustable component and the electrical parameter detection circuit. In this way, portability for detection of the wrist circumference data is improved, and the costs of the wrist circumference data are reduced.

With reference to the second aspect, in an implementation of the second aspect, the wrist fat thickness detection component includes:

an excitation electrode, a detection electrode, and an impedance detection circuit, where the excitation electrode is disposed on a side surface of the main body part and is configured to forward an excitation voltage, the detection electrode is disposed at a bottom of the main body part and is configured to receive a detection voltage, where the detection voltage is generated based on the excitation voltage and a voltage drop of wrist fat of the user, and the impedance detection circuit is disposed in the main body part and is configured to: generate the excitation voltage, and obtain the wrist fat thickness data through calculation based on the excitation voltage and the detection voltage.

The wrist fat thickness data is detected by using the excitation electrode, the detection electrode, and the impedance detection circuit. A non-traumatic wrist fat thickness data detection manner is provided, and accuracy of the wrist fat thickness data is improved.

With reference to the second aspect, in an implementation of the second aspect, the blood pressure detection component includes:

an air pump, an airbag, and a pressure sensor, where the air pump and the pressure sensor are disposed in the main body part, the airbag is disposed on a second surface of the strap, and the second surface is a contact surface of the strap with the wrist when the blood pressure detection apparatus is worn on the wrist of the user, the air pump is connected to the airbag, and the airbag is connected to the pressure sensor.

The air pump is configured to inflate the airbag. The pressure sensor is configured to: in a process of inflating the airbag, detect air pressure in the airbag in real time, and obtain the blood pressure data through calculation based on the air pressure.

With reference to the second aspect, in an implementation of the second aspect, the blood pressure detection apparatus further includes:

an indication component, where the indication component is disposed on a third surface of the main body part, the indication component is connected to the processor, the third surface is a surface away from the wrist when the blood pressure detection apparatus is worn on the wrist of the user, and the indication component is configured to prompt a health condition of the user by using an indication signal.

The health condition of the user is prompted by using the indication signal, to intuitively indicate the health condition of the user and improve user experience of the blood pressure detection apparatus.

According to a third aspect, an embodiment of this application provides an electronic device, including a memory, a processor, and a computer program that is stored in the memory and that can be run on the processors. The blood pressure detection method according to any implementation of the first aspect is implemented when the processor executes the computer program.

According to a fourth aspect, an embodiment of this application provides a computer-readable storage medium. The computer-readable storage medium stores a computer program. The blood pressure detection method according to any implementation of the first aspect is implemented when a processor executes the computer program.

According to a fifth aspect, an embodiment of this application provides a computer program product. When the computer program product is run on an electronic device, the electronic device is enabled to perform the blood pressure detection method according to any implementation of the first aspect.

It may be understood that, for the beneficial effects of the second aspect to the fifth aspect, refer to the related description in the first aspect. Details are not described herein again.

In embodiments of this application, the wearable device corrects the blood pressure data based on the wrist circumference data and the wrist fat thickness data, to avoid an impact of a wrist circumference size and a wrist fat thickness on blood pressure measurement, thereby improving accuracy of blood pressure measurement. In addition, the same airbag can be adapted to different people with different wrist circumferences and different wrist fat thicknesses. Blood pressure data can be accurately detected for different users without replacing different types of airbags, to improve compatibility of the blood pressure measurement apparatus and enhance user wearing experience.

DETAILED DESCRIPTION OF ILLUSTRATIVE EMBODIMENTS

Figure 1:
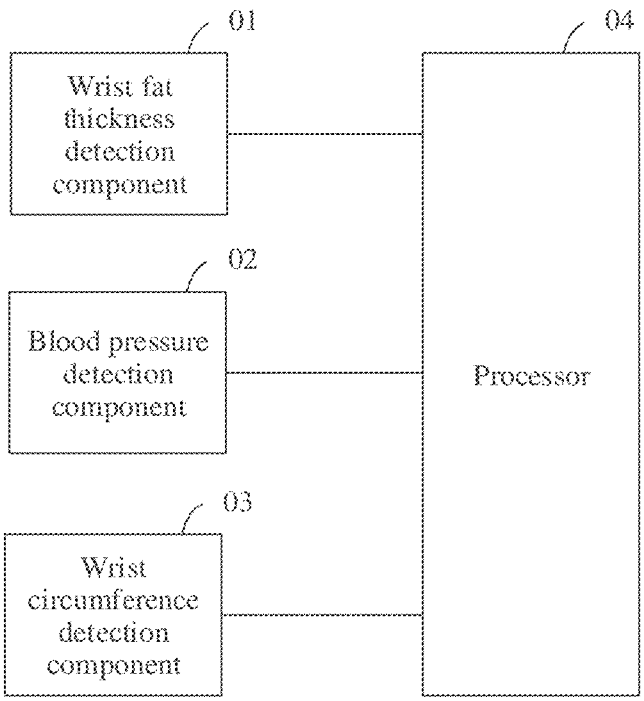
FIG. 1 is a block diagram of a module principle of a blood pressure detection apparatus according to an embodiment of this application.

In the following description, to illustrate rather than limit, specific details such as a particular system structure and a technology are provided to make a thorough understanding of embodiments of this application. However, persons skilled in the art should know that this application may be practiced in other embodiments without these specific details. In other cases, detailed descriptions of well-known systems, apparatuses, circuits, and methods are omitted, so that this application is described without being obscured by unnecessary details.

It should be understood that the term "include" used in this specification and the appended claims in this application specifies presence of features, integers, steps, operations, elements, and/or components, with presence or addition of one or more other features, integers, steps, operations, elements, components, and/or their combinations not excluded.

It should be further understood that the term "and/or" used in this specification and the appended claims in this application means any combination of one or more of the associated listed items and all possible combinations and includes these combinations.

According to the context, the term "if" used in this specification and the appended claims in this application may be interpreted as a meaning of "when" or "once" or "in response to determining" or "in response to detecting". Similarly, according to the context, the phrase "if it is determined that" or "if (a stated condition or event) is detected" may be interpreted as a meaning of "once it is determined that" or "in response to determining" or "once (a stated condition or event) is detected" or "in response to detecting (a stated condition or event)".

In addition, in the description of this specification and the appended claims in this application, the terms "first", "second", "third", and the like are merely used to distinguish the description, and cannot be construed as indicating or implying relative importance.

Reference to "an embodiment", "some embodiments", or the like described in this specification in this application indicates that one or more embodiments of this application include a specific feature, structure, or characteristic described with reference to embodiments. Therefore, statements such as "in an embodiment", "in some embodiments", "in some other embodiments", and "in other embodiments" that appear at different places in this specification do not necessarily mean referring to a same embodiment. Instead, the statements mean "one or more but not all of embodiments", unless otherwise specifically emphasized in another manner. The terms "include", "contain", "have", and their variants all mean "include but are not limited to", unless otherwise specifically emphasized in another manner.

The blood pressure detection method provided in this embodiment of this application may be applied to an electronic device, for example, a wearable device. A specific type of the wearable device is not limited in embodiments of this application.

As an example instead of limitation, when the electronic device is a wearable device, the wearable device may be a generic term of wearable devices, for example, glasses, gloves, watches, clothes, and shoes, developed through implementing an intelligent design on daily wear by using a wearable technology. The wearable device is a portable device that is directly worn on a body or integrated into clothes or an accessory of a user. The wearable device is not merely a hardware device, but is used to implement a powerful function through software support, data interaction, and cloud interaction. In a board sense, wearable intelligent devices include full-featured and large-sized devices that can implement complete or partial functions without depending on smartphones, for example, smart watches or smart glasses, and devices that focus on only one type of application function and need to work with other devices such as smartphones, such as various smart bands, smart watches, or smart jewelry for monitoring physical signs.

FIG. 1 shows a structure of a blood pressure detection apparatus provided in an embodiment of this application. For ease of description, only a part related to this embodiment of the present invention is shown. Details are as follows:

The blood pressure detection apparatus includes: a wrist circumference detection component 03, a wrist fat thickness detection component 01, a blood pressure detection component 02, and a processor 04. The processor 04 is separately connected to the wrist circumference detection component 03, the wrist fat thickness detection component 01, and the blood pressure detection component 02.

The wrist circumference detection component 03 is configured to obtain wrist circumference data of a user. The wrist fat thickness detection component 01 is configured to obtain wrist fat thickness data of the user. The blood pressure detection component 02 is configured to obtain blood pressure data of the user. The processor 04 is configured to correct the blood pressure data based on the wrist circumference data and the wrist fat thickness data.

The processor 04 is specifically configured to: determine, based on the wrist circumference data and the wrist fat thickness data, whether the blood pressure data needs to be corrected; and when the blood pressure data needs to be corrected, obtain, from a preset database, a mapping relationship corresponding to the wrist circumference data and the wrist fat thickness data, and correct the blood pressure data based on the mapping relationship.

The blood pressure detection apparatus includes: a main body part and a strap connected to the main body part. The strap is configured to wear the main body part on a wrist of the user. The processor 04 is disposed in the main body part.

Figure 2:
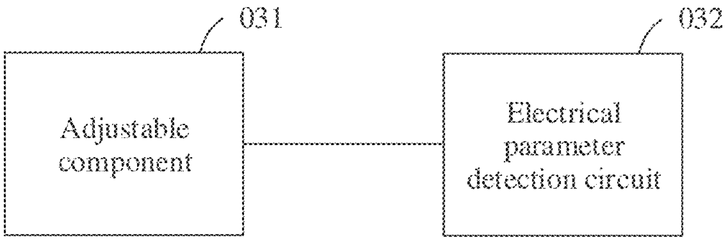
FIG. 2 is a block diagram of a module principle of a wrist circumference detection circuit in a blood pressure detection apparatus according to an embodiment of this application.
Figure 3:
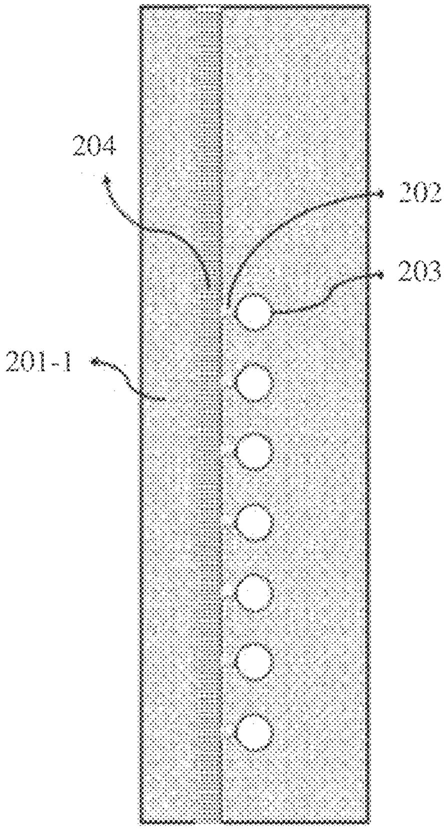
FIG. 3 is a schematic diagram of a structure of an embedded adjustable component of a first strap in a buckle design of a blood pressure detection apparatus according to an embodiment of this application.
Figure 4:
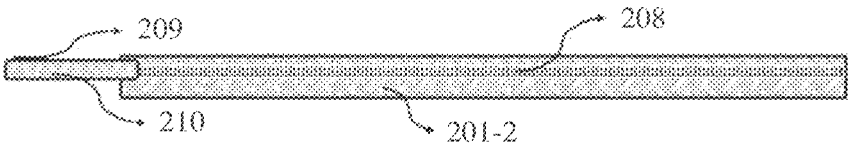
FIG. 4 is a side view of a second strap in a buckle design of a blood pressure detection apparatus according to an embodiment of this application.
Figure 5:
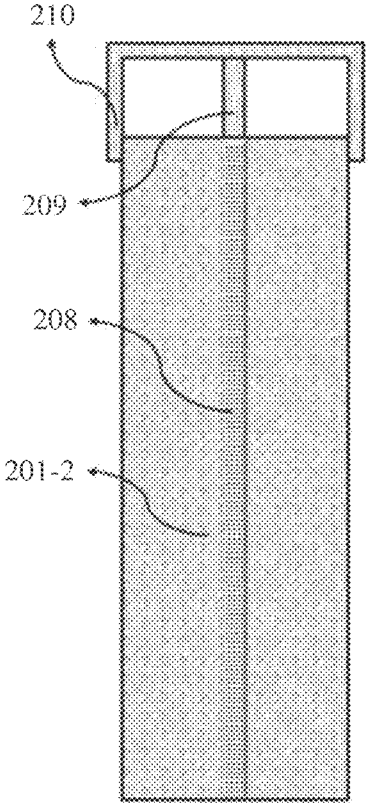
FIG. 5 is a front view of a second strap in a buckle design of a blood pressure detection apparatus according to an embodiment of this application.
Figure 6:
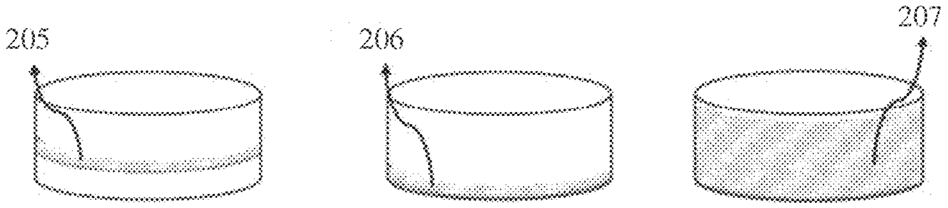
FIG. 6 is a schematic diagram of a structure of holes in a strap in a buckle design of a blood pressure detection apparatus according to an embodiment of this application.

As shown in FIG. 2, the wrist circumference detection component 03 includes an adjustable component 031 and an electrical parameter detection circuit 032. The adjustable component 031 is connected to the electrical parameter detection circuit 032. The electrical parameter detection circuit 032 is disposed in the main body part and is configured to: detect an electrical parameter of the adjustable component, and obtain, based on a preset correspondence between the electrical parameter and the wrist circumference data, wrist circumference data corresponding to the detected electrical parameter.

In an implementation, the strap may use a buckle design. For example, in FIG. 3 to FIG. 6, the strap includes a first strap 201-1 and a second strap 201-2. The first strap 201-1 and the second strap 201-2 are separately connected to the main body part. The adjustable component 204 is disposed on a first surface of the first strap 201-1. The first surface is a surface close to the wrist when the blood pressure detection apparatus is worn on the wrist of the user. The first strap 201-1 is further provided with a plurality of holes 203 parallel to the adjustable component 204. The adjustable component 204 is connected to the holes 203 through a first conducting wire 202. The second strap 201-2 is provided with a buckle tongue 209 matching the holes 203. A second conducting wire 205 is disposed on both surfaces of the buckle tongue 209 and the holes 203. When the buckle tongue 209 is connected to the holes 203 through the second conducting wire 205, an electrical parameter of the adjustable component 204 may be adjusted based on a position of the buckle tongue 209.

Figure 7:
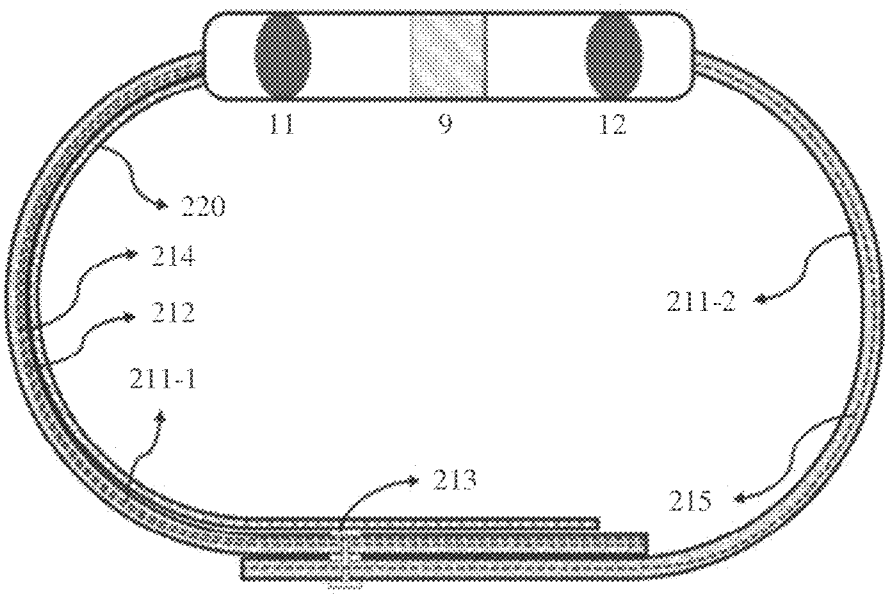
FIG. 7 is a side view of a strap in a butterfly clasp design of a blood pressure detection apparatus according to an embodiment of this application.
Figure 8:
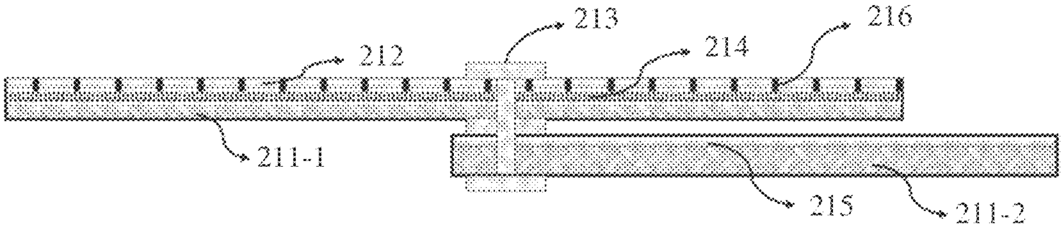
FIG. 8 is an enlarged schematic diagram of a butterfly clasp 213 in FIG. 18.
Figure 9:
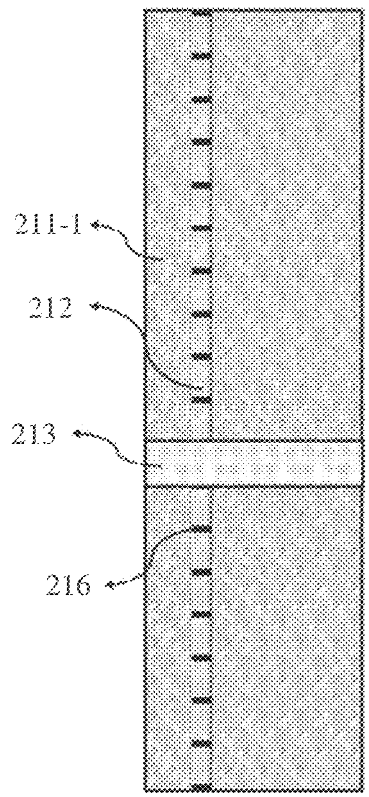
FIG. 9 is a front view of a strap in a butterfly clasp design of a blood pressure detection apparatus according to an embodiment of this application.

In another implementation, the strap may alternatively use a butterfly clasp design. For example, in FIG. 7 to FIG. 9, the strap includes a first strap 211-1 and a second strap 211-2. The first strap 211-1 and the second strap 211-2 are separately connected to the main body part. The adjustable component 214 is disposed on a first surface of the first strap 211-2. The first surface is a surface close to the wrist when the blood pressure detection apparatus is worn on the wrist of the user. An insulator 212 is disposed on a surface of the adjustable component 214. A plurality of third conducting wires 216 are embedded in the insulator 212 in a spaced manner and connected to the adjustable component 214. A movable butterfly clasp 213 is disposed on the second strap 211-2. The butterfly clasp 213 is connected to the adjustable component 214 through the third conducting wires 216. When the butterfly clasp 213 moves on the strap, an electrical parameter of the adjustable component 214 may be adjusted based on a position of the butterfly clasp 213.

Optionally, the adjustable component includes at least one of an adjustable resistor, an adjustable capacitor, and an adjustable inductor.

Figure 10:
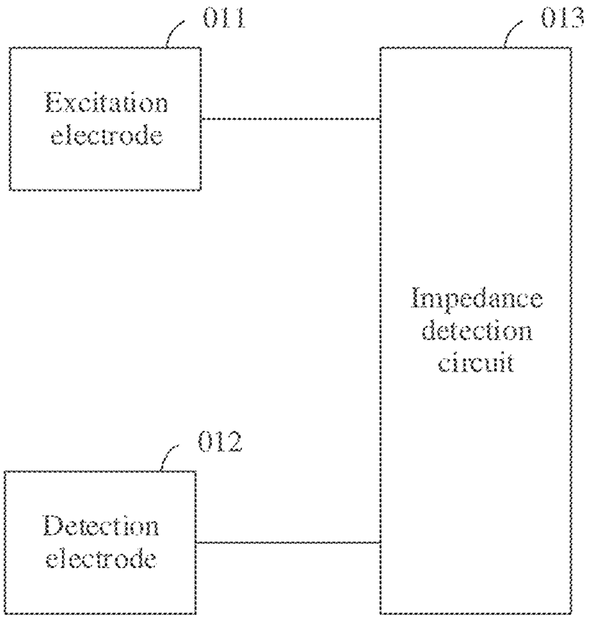
FIG. 10 is a block diagram of another module principle of a wrist fat thickness detection circuit in a blood pressure detection apparatus according to an embodiment of this application.

As shown in FIG. 10, the wrist fat thickness detection component 01 includes an excitation electrode on, a detection electrode 012, and an impedance detection circuit 013.

Figure 11:
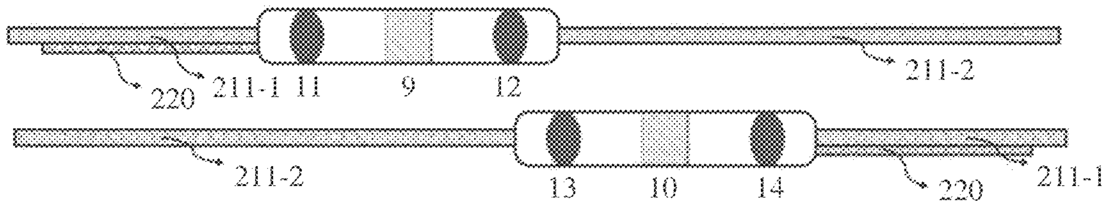
FIG. 11 is a schematic diagram of a structure of side electrodes of a main body part of a blood pressure detection apparatus according to an embodiment of this application.
Figure 23:
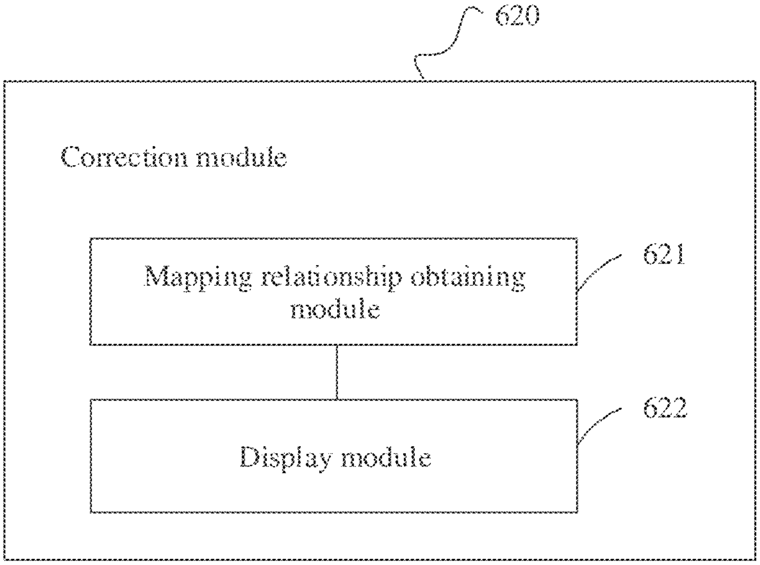
FIG. 23 is a schematic diagram of another structure of a correction module in a blood pressure detection apparatus according to an embodiment of this application.

As shown in FIG. 11, the excitation electrode on is disposed on a side surface of the main body part and is configured to forward an excitation voltage. As shown in FIG. 23, the detection electrode 012 is disposed at a bottom of the main body part and is configured to receive a detection voltage. The detection voltage is generated based on the excitation voltage and a voltage drop of wrist fat of the user. The impedance detection circuit 013 is disposed in the main body part and is configured to: generate the excitation voltage, and obtain the wrist fat thickness data through calculation based on the excitation voltage and the detection voltage.

A non-adipose tissue has relatively low electrical impedance because the non-adipose tissue contains many electrolytes and water. An adipose tissue is anhydrous and has relatively high electrical impedance. The impedance detection circuit 013 obtains bioelectrical impedance based on the excitation voltage and the detection voltage. The voltage drop of the wrist fat of the user indicates an electric potential difference generated due to the bioelectrical impedance. The impedance detection circuit 013 may further obtain the wrist circumference fat thickness data based on the bioelectrical impedance.

Figure 12:
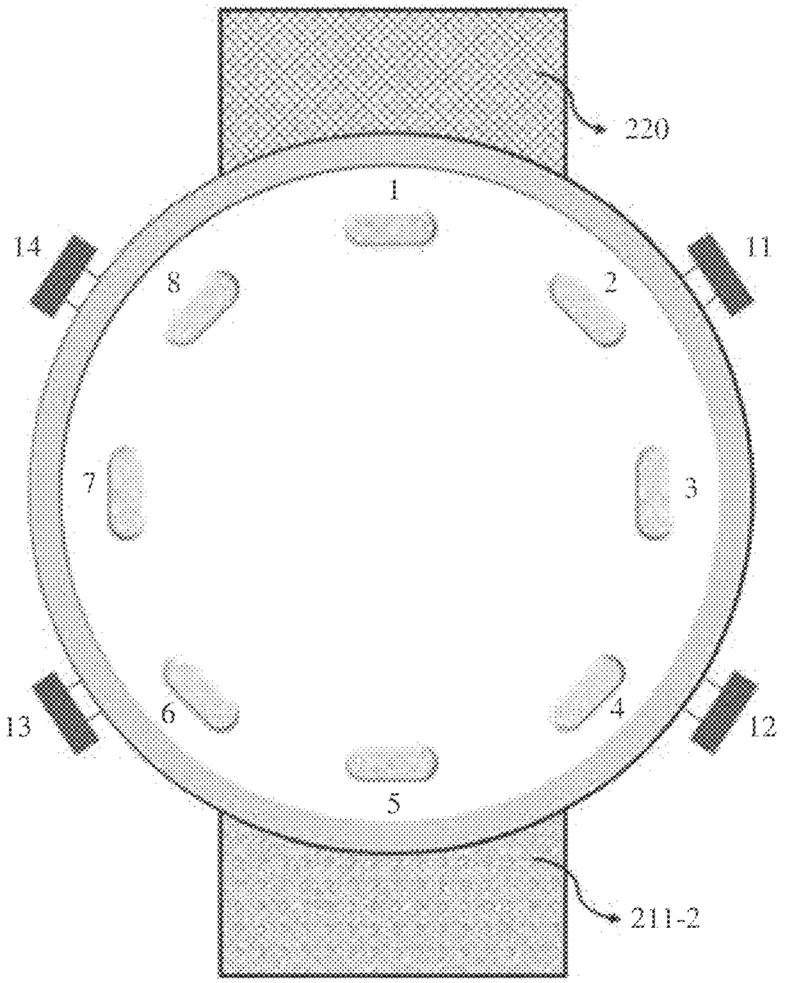
FIG. 12 is a schematic diagram of a structure of bottom electrodes of a main body part of a blood pressure detection apparatus according to an embodiment of this application.

Optionally, as shown in FIG. 11 and FIG. 12, there are a plurality of excitation electrodes on. The excitation electrodes on are sequentially arranged on the side surface of the main body part. There are a plurality of detection electrodes 012. The detection electrodes 012 are disposed at the bottom of the main body part and are sequentially arranged along the periphery of the bottom of the main body part. Each excitation electrode is connected to one detection electrode.

The plurality of excitation electrodes on and the plurality of detection electrodes 012 are disposed, so that the impedance detection circuit 013 can generate a wrist fat thickness detection signal based on a plurality of excitation voltages and a plurality of detection voltages, to more accurately determine the wrist fat thickness data, thereby improving accuracy of blood pressure detection.

In FIG. 11 and FIG. 12, a button 11, a button 12, a button 13, and a button 14 are separately disposed on the side surface of the main body part. Eight detection electrodes disposed at the bottom of the main body part are respectively a detection electrode 1, a detection electrode 2, a detection electrode 3, a detection electrode 4, a detection electrode 5, a detection electrode 6, a detection electrode 7, and a detection electrode 8. Two excitation electrodes are respectively disposed on left and right side of the main body part, respectively: an excitation electrode 9 and an excitation electrode 10. The detection electrode 1, the detection electrode 3, the detection electrode 5, and the detection electrode 7 are connected to form a first group of detection electrodes; and the detection electrode 2, the detection electrode 4, the detection electrode 6, and the detection electrode 8 are connected to form a second group of detection electrodes. The first group of detection electrodes are connected to the excitation electrode 9 by using the human body of the user, and the second group of detection electrodes are connected to the excitation electrode 10 by using the human body of the user.

It is assumed that the blood pressure detection apparatus is worn on the left hand, the electrode at the bottom of the main body part of the blood pressure detection apparatus is in contact with the left wrist, and two fingers of the right hand are in contact with two electrodes on the side surface of the main body part. In this case, the human body accesses a circuit. Due to conductivity of the human body, the first group of detection electrodes are connected to the excitation electrode 9 by using the human body of the user, and the second group of detection electrodes are connected to the excitation electrode 10 by using the human body of the user to form a loop. In addition, impedance of the human body is not 0. Therefore, there is an electric potential difference between electrodes. The impedance detection circuit 013 may calculate the wrist fat thickness data based on an electric potential difference between each of the plurality of excitation voltages and each of the plurality of detection voltages.

It should be noted that a position of the excitation electrode 011 and a position of the detection electrode 012 may be interchanged. The plurality of excitation electrodes 011*i* may also be disposed at the bottom of the main body part of the blood pressure detection apparatus and sequentially arranged along the periphery of the bottom of the main body part of the blood pressure detection apparatus. The plurality of groups of detection electrodes 012*i* may also be sequentially arranged on the side surface of the main body part of the blood pressure detection apparatus.

In another implementation, the wrist fat thickness detection circuit 01 includes at least one of an optical sensor or an ultrasonic sensor.

The wrist fat thickness detection circuit 01 may transmit a first ultrasonic wave to the wrist of the user, and record transmit time of the first ultrasonic wave. When receiving a second ultrasonic wave, the wrist fat thickness detection circuit 01 records receive time of the second ultrasonic wave. The second ultrasonic wave is an ultrasonic wave reflected after the first ultrasonic wave reaches the bone of the wrist. The wrist fat thickness detection circuit 01 determines the wrist fat thickness data based on the transmit time of the first ultrasonic wave and the receive time of the second ultrasonic wave.

It should be noted that the blood pressure detection component includes an air pump, an airbag, and a pressure sensor.

The air pump and the pressure sensor are disposed in the main body part. As shown in FIG. 11 and FIG. 12, the airbag 220 is disposed on a second surface of the strap 211-1. The second surface is a contact surface of the strap with the wrist when the blood pressure detection apparatus is worn on the wrist of the user. The air pump is connected to the airbag 220. The airbag 220 is connected to the pressure sensor. The air pump is configured to inflate the airbag 220. The pressure sensor is configured to: detect air pressure in the airbag in real time in an inflation process of the airbag 220, and obtain the blood pressure data through calculation based on the air pressure.

Figure 13:
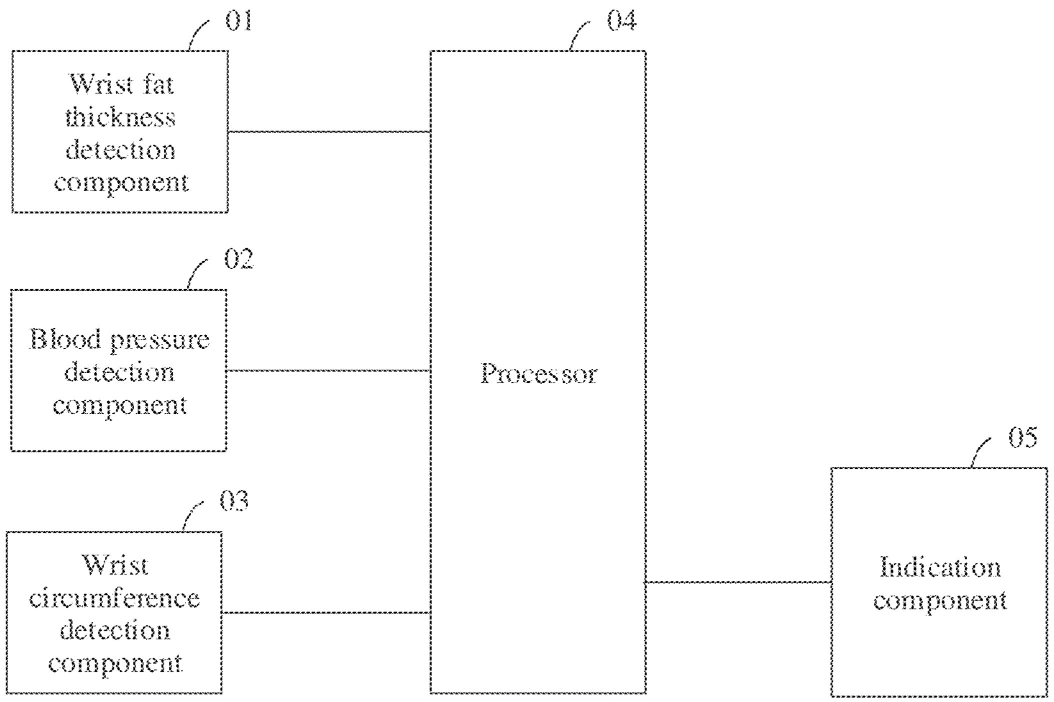
FIG. 13 is a block diagram of another module principle of a blood pressure detection apparatus according to an embodiment of this application.

Optionally, as shown in FIG. 13, the blood pressure detection apparatus further includes an indication component 05. The indication component 05 is disposed on a third surface of the main body part. The indication component 05 is connected to the processor 04. The third surface is a surface away from the wrist when the blood pressure detection apparatus is worn on the wrist of the user. The indication component is configured to indicate a health condition of the user by using an indication signal.

The indication component 05 may include a plurality of LEDs. The LEDs blink or glow to indicate whether target blood pressure, a heart rate, and a body fat thickness coefficient of the user are normal. Alternatively, different health conditions may be indicated by using colors (red, orange, yellow, green, and the like) of the LEDs. For example, a red LED indicates a serious problem of the body of the user, an orange LED indicates a relatively large problem of the body of the user, a yellow LED indicates a slight problem of the body of the user, and a green LED indicates a good health condition of the body of the user.

The blood pressure detection apparatus may be a blood pressure wrist strap, a wrist sphygmomanometer, or a blood pressure watch.

A blood pressure detection method provided in an embodiment of this application is described below in detail. With reference to a flowchart of a blood pressure detection method shown in FIG. 14, the method includes the following content.

Figure 14:
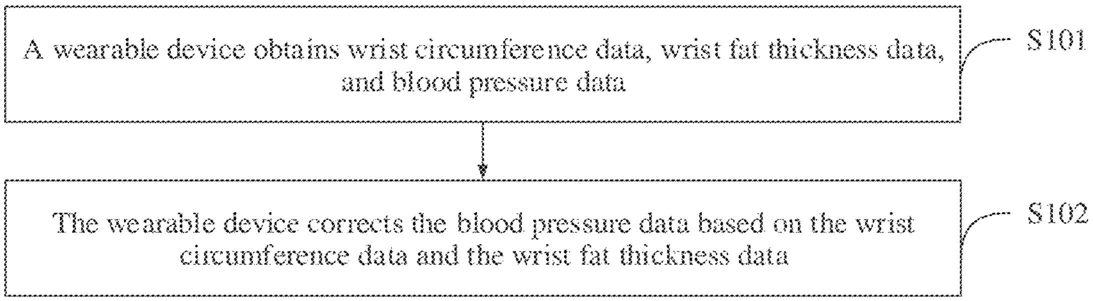
FIG. 14 is a schematic flowchart of a blood pressure detection method according to an embodiment of this application.

FIG. 14 is a schematic flowchart of a blood pressure detection method according to this application. As an example instead of limitation, the method may be applied to the foregoing electronic device. The blood pressure detection method includes the following steps:

S101: A wearable device obtains wrist circumference data, wrist fat thickness data, and blood pressure data.

Specifically, the wrist circumference data may be a product of a wrist circumference length and a preset coefficient.

In a possible implementation, that the wearable device obtains the wrist circumference data of a user may include:

S101-1*a:* The wearable device detects an electrical parameter of an adjustable component around a wrist of the user. The adjustable component includes at least one of an adjustable resistor, an adjustable capacitor, or an adjustable inductor.

The adjustable component may be disposed in a strap of the electronic device or at a first surface of a strap of the electronic device, and may adjust the electrical parameter of the adjustable component based on a position of a buckle or a butterfly clasp of the strap.

In specific implementation, detection of the electrical parameter includes two cases. In a first case, a constant voltage source is used as a power supply. Different currents flow through the adjustable component in cases of different positions of the buckle or the butterfly clasp of the strap, to obtain different electrical parameters. In a second case, a constant current source is used as a power supply. Different electric potential differences between two ends of the adjustable component are obtained in cases of different positions of the buckle or the butterfly clasp of the strap, to obtain different electrical parameters.

For example, when the electronic device is a wrist electronic device, the electronic device includes a main body part and a strap connected to the main body part. The strap is used to wear the electronic device on the wrist of the user. Optionally, a structural relationship between the adjustable component and the strap is shown in FIG. 3 to FIG. 9.

S101-2*a:* Obtain wrist circumference data corresponding to the electrical parameter.

Specifically, the wrist circumference data corresponding to the electrical parameter may be obtained from a second preset database, or the wrist circumference data corresponding to the electrical parameter may be obtained based on a function relationship.

It should be noted that the adjustable component may include at least one of an adjustable resistor, an adjustable capacitor, and an adjustable inductor. The electrical parameter includes at least one of a capacitance value, a resistance value, and an inductance value.

Figure 15:
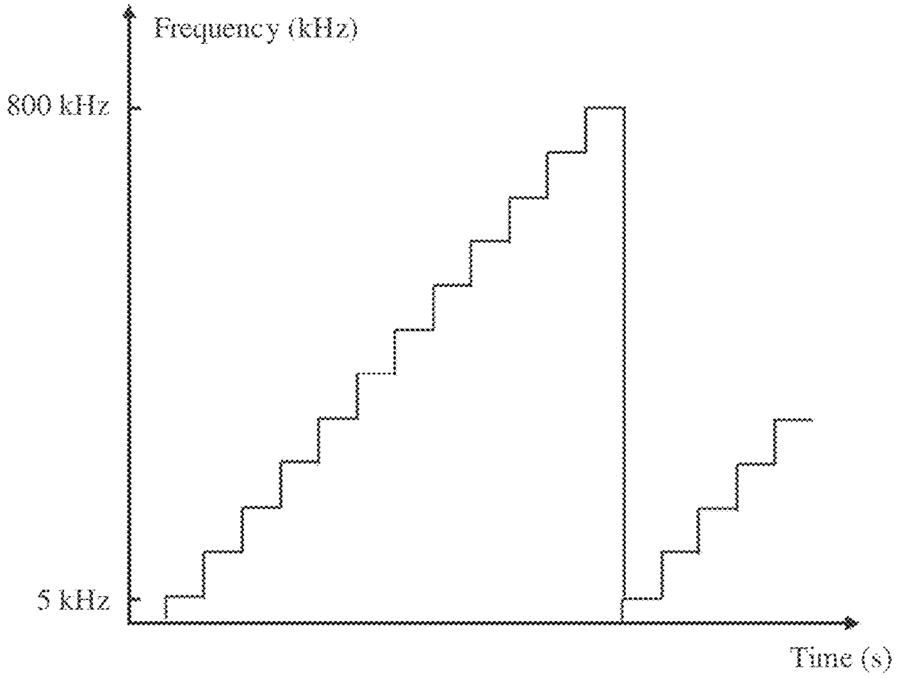
FIG. 15 is a relationship diagram indicating that a frequency of a test current changes with time in a process of performing impedance detection on a wrist of a user to obtain wrist fat thickness data.

Two possible implementations of obtaining the wrist fat thickness coefficient are specifically as follows:

In a possible implementation, impedance detection is performed on the human body of the user to obtain a wrist fat thickness coefficient. Specifically, test currents on a plurality of frequencies are input to the user; a plurality of electric potential differences formed in the human body by the test currents on the plurality of frequencies are detected; and the wrist fat thickness data is determined based on the plurality of test currents and the plurality of electric potential differences. FIG. 15 is a relationship diagram indicating that a frequency of a test current changes with time. In FIG. 15, an X-axis represents time, and a Y-axis represents a frequency of a test current.

A non-adipose tissue has relatively low electrical impedance because the non-adipose tissue contains many electrolytes and water. An adipose tissue is anhydrous and has relatively high electrical impedance. In addition, when a direct current or a low-frequency current enters a biological tissue, the current bypasses cells and mainly flows through extracellular fluid. With an increase of a frequency of the current, the current may pass through cell membranes and flow through intracellular fluid. Therefore, the bioelectrical impedance of the wrist of the user changes with the frequency. The plurality of frequencies and an impedance spectrum corresponding to the plurality of frequencies indicate abundant impedance and human body composition information. Therefore, bioelectrical impedance on different frequencies may be obtained based on the plurality of test currents and the plurality of electric potential differences. In this way, the wrist fat thickness data may be determined based on the bioelectrical impedance on different frequencies.

In another possible implementation, ultrasonic distance detection is performed on the wrist of the user to obtain the wrist fat thickness data. A first ultrasonic wave is transmitted to the wrist of the user, and transmit time of the first ultrasonic wave is recorded. When a second ultrasonic wave is received, receive time of the second ultrasonic wave is recorded. The second ultrasonic wave is an ultrasonic wave reflected after the first ultrasonic wave reaches the bone of the wrist. The wrist fat thickness data is determined based on the transmit time of the first ultrasonic wave and the receive time of the second ultrasonic wave.

It should be noted that the wrist circumference data and the wrist fat thickness data may be data detected in real time. For example, when blood pressure detection information is triggered, current wrist circumference data and current wrist fat thickness data of the user are detected.

Preferably, because the wrist circumference data and the wrist fat thickness data of the user change slightly in relatively short time, a time interval may be set, so that the wrist circumference data and the wrist fat thickness data of the user are detected when a specific time interval is reached, and the detected wrist circumference data and the detected wrist fat thickness data are stored. When a next time interval is reached, the wrist circumference data and the wrist fat thickness data that are previously stored are replaced with latest detected wrist circumference data and latest detected wrist fat thickness data. When blood pressure detection information is triggered, the wrist circumference data and the wrist fat thickness data are directly obtained in a storage position.

Finally, the blood pressure data of the user may be obtained by using a sphygmomanometer. Specifically, an air pressure sensor connected to an airbag measures air pressure in the airbag, separates a pulse wave signal from the air pressure, and performs a series of processing on the pulse wave signal, for example, extracts a pulse wave envelope feature and a single pulse wave feature to obtain a feature parameter, and calculates the blood pressure data based on the feature parameter.

S102: The wearable device corrects the blood pressure data based on the wrist circumference data and the wrist fat thickness data.

S102-1: When the wearable device determines, based on the wrist circumference data and the wrist fat thickness data, that the blood pressure data needs to be corrected, the wearable device obtains, from a preset database, a mapping relationship corresponding to the wrist circumference data and the wrist fat thickness data.

Specifically, if the wrist circumference data is not less than preset wrist circumference data and/or the wrist fat thickness data is not less than preset wrist fat thickness data, the wearable device determines that the blood pressure data needs to be corrected.

Step S102-1 may be specifically as follows:

When the wrist fat thickness data is less than a first preset wrist fat thickness, and the wrist circumference data is less than a second wrist circumference, the wearable device determines that the blood pressure data does not need to be corrected.

When the wrist fat thickness data is greater than the first preset wrist fat thickness, and the wrist circumference data is less than a first wrist circumference, the wearable device determines that the blood pressure data does not need to be corrected.

When the wrist fat thickness data is less than the first preset wrist fat thickness, and the wrist circumference data is greater than the second wrist circumference, the wearable device determines that the blood pressure data needs to be corrected.

When the wrist fat thickness data is less than a second preset wrist fat thickness and greater than the first preset wrist fat thickness, and the wrist circumference data is greater than the first wrist circumference and less than the second wrist circumference, the wearable device determines that the blood pressure data needs to be corrected.

When the wrist fat thickness data is less than the second preset wrist fat thickness and greater than the first preset wrist fat thickness, and the wrist circumference data is greater than the second wrist circumference, the wearable device determines that the blood pressure data needs to be corrected.

When the wrist fat thickness data is greater than the second preset wrist fat thickness and greater than the first preset wrist fat thickness, and the wrist circumference data is greater than the first wrist circumference, the wearable device determines that the blood pressure data needs to be corrected.

The first preset wrist fat thickness is less than the second preset wrist fat thickness, and the first wrist circumference is less than the second wrist circumference. The first wrist circumference may be 150 mm, and the second wrist circumference may be 180 mm.

After determining that the blood pressure data needs to be corrected, the wearable device obtains, from the preset database, the mapping relationship matching the wrist circumference data and the wrist fat thickness data. The mapping relationship in the preset database is in one-to-one correspondence with wrist circumference data and wrist fat thickness data.

S102-2: The wearable device corrects the blood pressure data based on the mapping relationship, and displays the corrected blood pressure data.

Specifically, a compensation value is obtained based on the mapping relationship. The blood pressure data is corrected based on the compensation value (a sum of the compensation value and the blood pressure data is used as the corrected blood pressure data). The corrected blood pressure data is displayed.

The mapping relationship may be a quadratic polynomial function or a cubic polynomial function.

For example, the mapping relationship may be $$y = a_1 x_1^2 + a_2 x_2^2 + a_3 x_1 x_2 + a_4 x_1 + a_5 x_2 + a_6.$$

Herein, y is the compensation value, $x^1$ is the wrist circumference data, $x^2$ is the wrist fat thickness data, and $a^1$, $a_2$, $a_3$, $a_4$, $a_5$, and $a_6$ are all constants.

Figure 16:
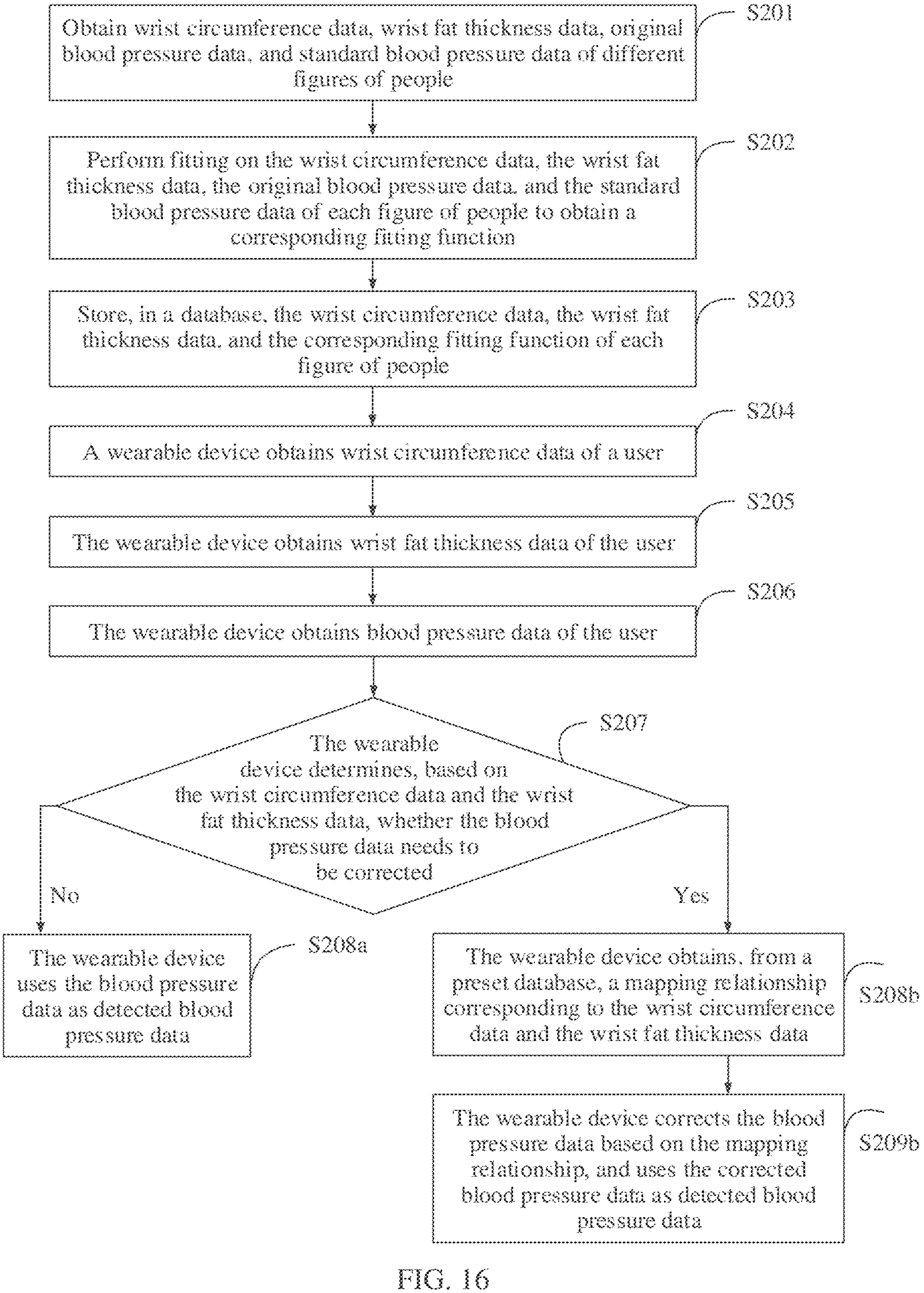
FIG. 16 is a schematic flowchart of another blood pressure detection method according to an embodiment of this application.

FIG. 16 is a schematic flowchart of another blood pressure detection method according to an embodiment of this application. Details are as follows:

S201: Obtain wrist circumference data, wrist fat thickness data, original blood pressure data, and standard blood pressure data of different figures of people.

First, a plurality of samples are selected for each figure of people. A plurality of pieces of wrist circumference data, wrist fat thickness data, original blood pressure data, and standard blood pressure data are separately measured. Then, data obtained in the experiment is screened to remove an unqualified sample. Finally, an average value is calculated for the plurality of pieces of original blood pressure data of each sample that are measured by a plurality of first sphygmomanometers, and an average value is calculated for the plurality of pieces of standard blood pressure data of each sample that are measured by a plurality of second sphygmomanometers, to form a data point on a calibration curve. The first sphygmomanometer uses a common airbag. The second sphygmomanometer uses an airbag adapted to the wrist circumference data and the wrist fat thickness data of the user; or the second sphygmomanometer is a mercury sphygmomanometer, or a medical arm-type electronic sphygmomanometer. Types of different figures of people include at least one of skin color, gender, age, height, weight, wrist circumference, blood pressure, and various diseases.

S202: Perform fitting on the wrist circumference data, the wrist fat thickness data, the original blood pressure data, and the standard blood pressure data of each figure of people to obtain a corresponding mapping relationship.

A scatter chart is drawn based on the foregoing data points. A plurality of mapping relationships are obtained through function curve fitting based on different wrist circumference data and different wrist fat thickness data. The mapping relationship may be fitted to any function, including a linear function or a non-linear function.

S203: Store, in a database, the wrist circumference data, the wrist fat thickness data, and the corresponding mapping relationship of each figure of people.

The mapping relationship in the database is in one-to-one correspondence with wrist circumference data and wrist fat thickness data.

S204: The wearable device obtains the wrist circumference data of the user.

S205: The wearable device obtains the wrist fat thickness data of the user.

S206: The wearable device obtains the blood pressure data of the user.

S207: The wearable device determines, based on the wrist circumference data and the wrist fat thickness data, whether the blood pressure data needs to be corrected.

Specifically, it is determined whether the wrist circumference data is less than preset wrist circumference data, and whether the wrist fat thickness data is less than preset wrist fat thickness data.

S208*a:* If the blood pressure data does not need to be corrected, the wearable device uses the blood pressure data as detected blood pressure data.

Specifically, if the wrist circumference data is less than the preset wrist circumference data and the wrist fat thickness data is less than the preset wrist fat thickness data, the wearable device determines that the blood pressure data does not need to be corrected, and uses the blood pressure data as the detected blood pressure data.

S208*b:* If the blood pressure data needs to be corrected, the wearable device obtains, from a preset database, the mapping relationship corresponding to the wrist circumference data and the wrist fat thickness data.

The mapping relationship matching the wrist circumference data and the wrist fat thickness data is obtained from the preset database. The mapping relationship in the preset database is in one-to-one correspondence with wrist circumference data and wrist fat thickness data.

S209*b:* The wearable device corrects the blood pressure data based on the mapping relationship, and uses the corrected blood pressure data as detected blood pressure data.

Figure 17:
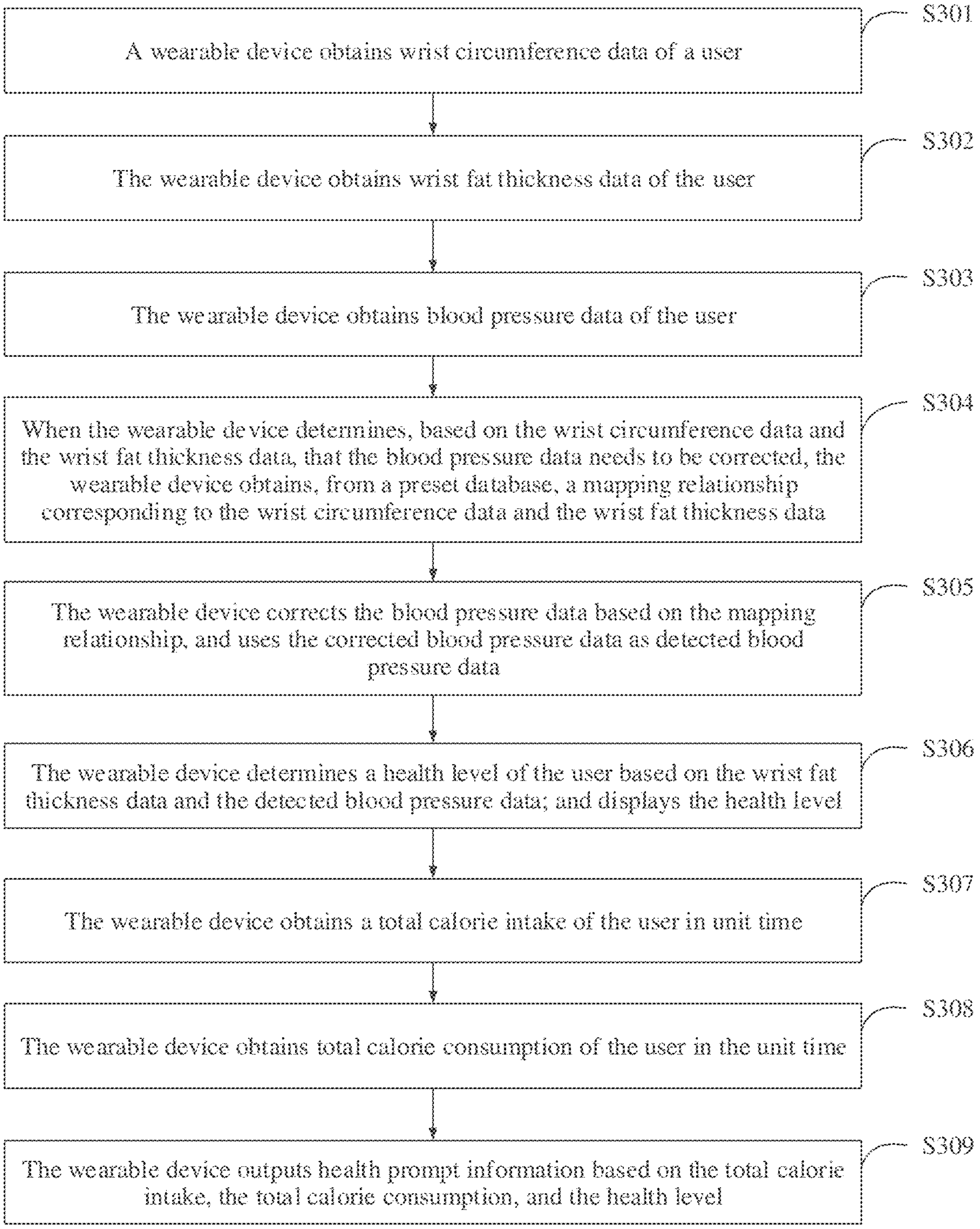
FIG. 17 is a schematic flowchart of another blood pressure detection method according to an embodiment of this application.

FIG. 17 is a schematic flowchart of another blood pressure detection method according to an embodiment of this application. Details are as follows:

S301: A wearable device obtains wrist circumference data of a user.

S302: The wearable device obtains wrist fat thickness data of the user.

S303: The wearable device obtains blood pressure data of the user.

S304: When the wearable device determines, based on the wrist circumference data and the wrist fat thickness data, that the blood pressure data needs to be corrected, the wearable device obtains, from a preset database, a mapping relationship corresponding to the wrist circumference data and the wrist fat thickness data.

S305: The wearable device corrects the blood pressure data based on the mapping relationship, and uses the corrected blood pressure data as detected blood pressure data.

S306: The wearable device determines a health level of the user based on the wrist fat thickness data and the detected blood pressure data; and displays the health level.

The health level may indicate a severe body problem, a large body problem, a slight body problem, and a good health condition.

Specifically, the health level corresponding to the blood pressure data and the wrist fat thickness data may be obtained from a third preset database.

Figure 18:
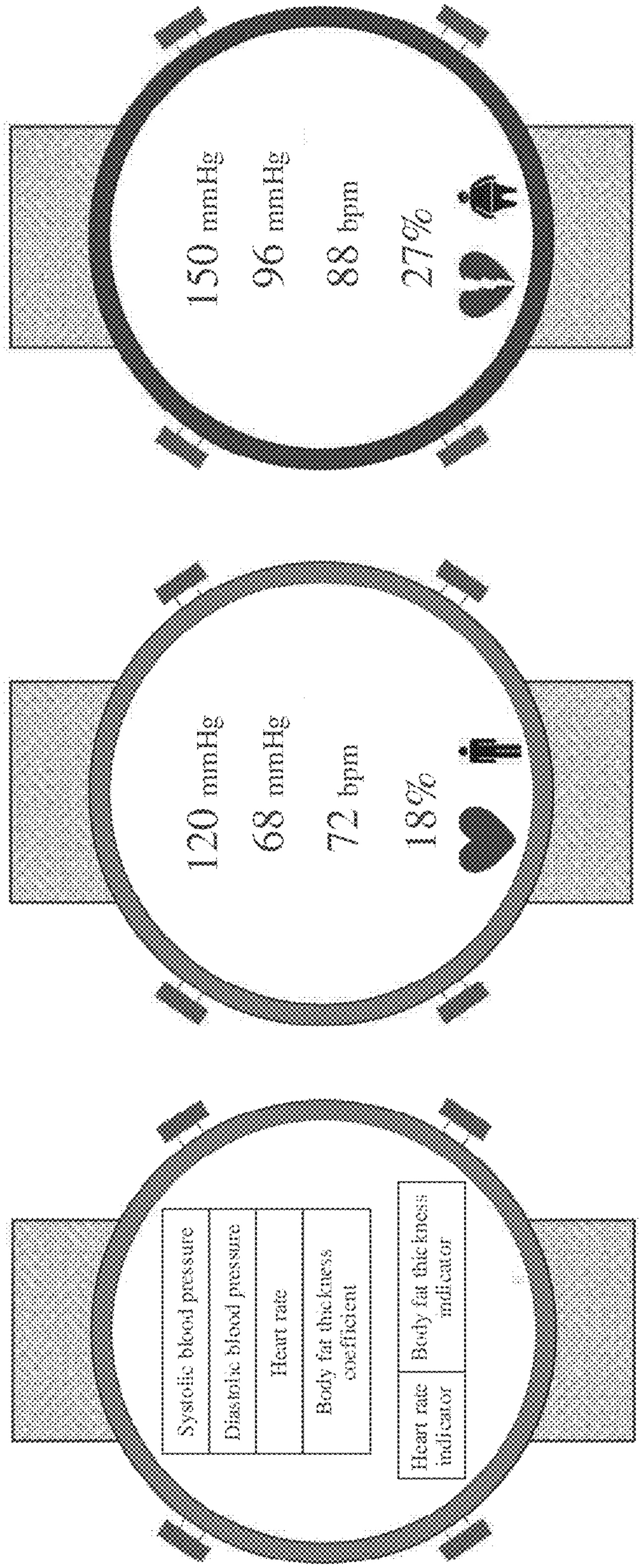
FIG. 18 is a schematic diagram of an interface for displaying a health level.

Optionally, coefficients such as a health level, target blood pressure, a heart rate, and a body fat thickness may be displayed in a manner of a chart, a table, an animation, and/or a text. For example, a schematic diagram of an interface for displaying a health level is shown in FIG. 18. A broken heart indicates that the user has arrhythmia, and a complete heart indicates that the user does not have arrhythmia. An icon of a thinner person indicates that the user has normal body fat, and an icon of a fatter person indicates that the user has relatively high body fat. Numbers from top to bottom indicate coefficients of systolic blood pressure, diastolic blood pressure, a heart rate, and a body fat thickness of the user. It should be noted that the foregoing body fat thickness coefficient may include a body fat percentage.

For example, LEDs may blink or glow to indicate whether the target blood pressure, the heart rate, and the body fat thickness coefficient of the user are normal. Alternatively, different health levels may be indicated by using colors (red, orange, yellow, green, and the like) of the LEDs. For example, a red LED indicates a serious problem of the body of the user, an orange LED indicates a relatively large problem of the body of the user, a yellow LED indicates a slight problem of the body of the user, and a green LED indicates a good health condition of the body of the user.

S307: The wearable device obtains a total calorie intake of the user in unit time.

Specifically, the total calorie intake that is of the user in the unit time and that is sent by a terminal may be obtained by using a wireless communications link. The total calorie intake of the user in the unit time is calculated based on a food image that is of the user in meals and that is photographed by the terminal and calories contained in each food.

The terminal is connected to the electronic device, converts a dietary record of the user into the total calorie intake, and sends the total calorie intake to the electronic device.

S308: The wearable device obtains total calorie consumption of the user in the unit time.

For example, motion status information of the user in the unit time may be obtained by using a motion detection sensor, and the total calorie consumption of the user may be calculated based on the motion status information.

S309: The wearable device outputs health prompt information based on the total calorie intake, the total calorie consumption, and the health level.

A difference between a total calorie intake value and total calorie consumption is used as a net calorie consumption value. A level difference is obtained based on a historical health level and the health level. The health prompt information corresponding to the net calorie consumption value and the level difference is obtained. The health prompt information is displayed. The health prompt information includes a health improvement level and a health improvement suggestion.

It should be understood that sequence numbers of the steps do not mean execution sequences in the foregoing embodiments. The execution sequences of the processes should be determined based on functions and internal logic of the processes, and should not be construed as any limitation on the implementation processes of embodiments of this application.

The following describes embodiments of the present invention in detail with a specific example. It should be noted that the example is merely used to help persons skilled in the art to understand embodiments of the present invention, instead of limiting embodiments of the present invention to the specific values or the specific scenarios in the example. Persons skilled in the art clearly can make various equivalent modifications or changes according to the examples described above, and such modifications or changes also fall within the scope of embodiments of the present invention.

It should be understood that the blood pressure watch in this example corresponds to the blood pressure detection apparatus in FIG. 14.

Figure 19:
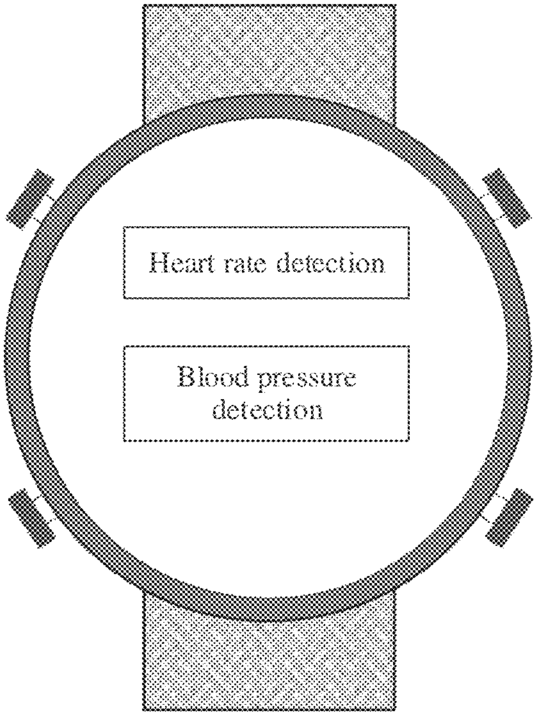
FIG. 19 is a schematic diagram of an interface of a blood pressure watch.

S190: A user presses a preset button of the blood pressure watch shown in FIG. 19, or a user triggers a "blood pressure detection" key in an interface of the blood pressure watch shown in FIG. 19. The blood pressure watch generates a detection instruction according to a button operation or a key operation.

S191: The blood pressure watch first detects, according to the detection instruction, an electrical parameter of an adjustable component around a wrist of the user, and obtains wrist circumference data corresponding to the electrical parameter. Specifically, the user adjusts a position of a buckle or a butterfly clasp of a strap based on a wrist circumference. The electrical parameter of the adjustable component is determined based on the position of the buckle or the butterfly clasp of the strap. For example, the blood pressure watch determines that the wrist circumference data is 181 mm.

S192: The blood pressure watch then inputs test currents on a plurality of frequencies to the user; detects a plurality of electric potential differences formed in the human body by the test currents on the plurality of frequencies; and obtains bioelectrical impedance on different frequencies based on the plurality of test currents and the plurality of electric potential differences, and determines wrist fat thickness data based on the bioelectrical impedance on different frequencies. For example, the blood pressure watch determines that the wrist fat thickness data is 4.5 mm.

S193: The blood pressure watch further obtains blood pressure data of the user. Specifically, the blood pressure watch obtains systolic blood pressure of the user: 140 mmHg, and obtains diastolic blood pressure of the user: 90 mmHg.

S194: The blood pressure watch determines, based on the wrist circumference data and the wrist fat thickness data, whether the blood pressure data needs to be corrected. Specifically, the blood pressure watch determines that the wrist fat thickness data is less than a second preset wrist fat thickness (for example, 5 mm) and greater than a first preset wrist fat thickness (for example, 2.5 mm), and that the wrist circumference data is greater than a second wrist circumference (for example, 180 mm). The blood pressure watch determines that the blood pressure data needs to be corrected.

S195: The blood pressure watch obtains, from a preset database, a fitting function corresponding to the wrist circumference data and the wrist fat thickness data.

S196: The blood pressure watch obtains a compensation value 4 mmHg by using a fitting function, corrects the blood pressure data based on the compensation value, uses the corrected blood pressure data (the systolic blood pressure of the user is 144 mmHg, and the diastolic blood pressure of the user is 94 mmHg) as detected blood pressure data, and displays the detected blood pressure data.

S197: The blood pressure watch determines a health level of the user based on the wrist fat thickness data and the detected blood pressure data, for example, 4; and displays the health level. For example, the health level is displayed on the interface. An orange LED is used to indicate a relatively large problem of the body of the user.

S198: The blood pressure watch obtains, by using a wireless communications link, a total calorie intake that is of the user within one day and that is sent by a terminal: 3200 Ka, and the blood pressure watch further obtains, by using a motion sensor, total calorie consumption of the user in unit time: 1589 Ka.

S199: The blood pressure watch uses a difference 1611 Ka between a total calorie intake value and total calorie consumption as a net calorie consumption value; and obtains a level difference: 1 based on a historical health level (level 3) and the health level, and obtains health prompt information corresponding to the net calorie consumption value 1611 Ka and the level difference: 1. For example, the health prompt information includes immediately measuring blood pressure by using a standard sphygmomanometer, taking a related medicament, reducing a calorie intake, and contacting a doctor. The blood pressure watch displays the health prompt information.

Figure 20:
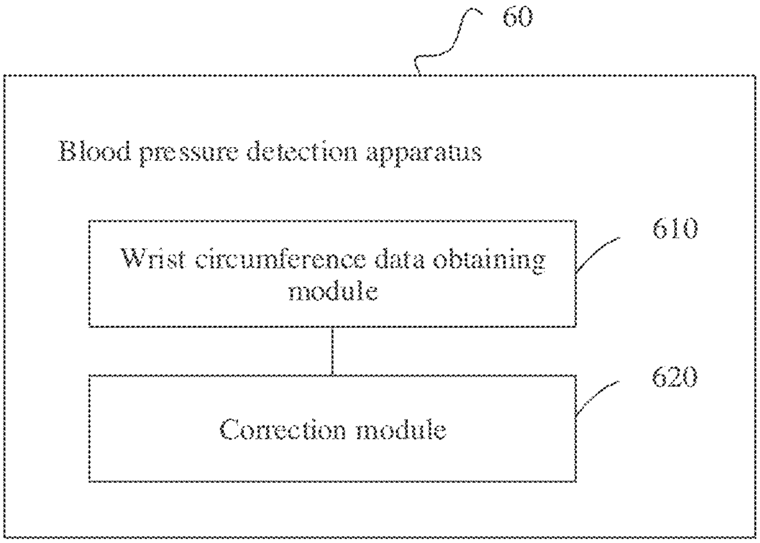
FIG. 20 is a schematic diagram of a structure of a blood pressure detection apparatus according to an embodiment of this application.

In correspondence with the blood pressure detection method in the foregoing embodiments, FIG. 20 is a block diagram of a structure of a blood pressure detection apparatus according to an embodiment of this application. For ease of description, only a part related to embodiments of this application is shown.

With reference to FIG. 20, the blood pressure detection apparatus 60 includes a wrist circumference data obtaining module 610 and a correction module 620.

The wrist circumference data obtaining module 610 is configured to obtain wrist circumference data, wrist fat thickness data, and blood pressure data.

The correction module 620 is configured to correct the blood pressure data based on the wrist circumference data and the wrist fat thickness data.

Figure 21:
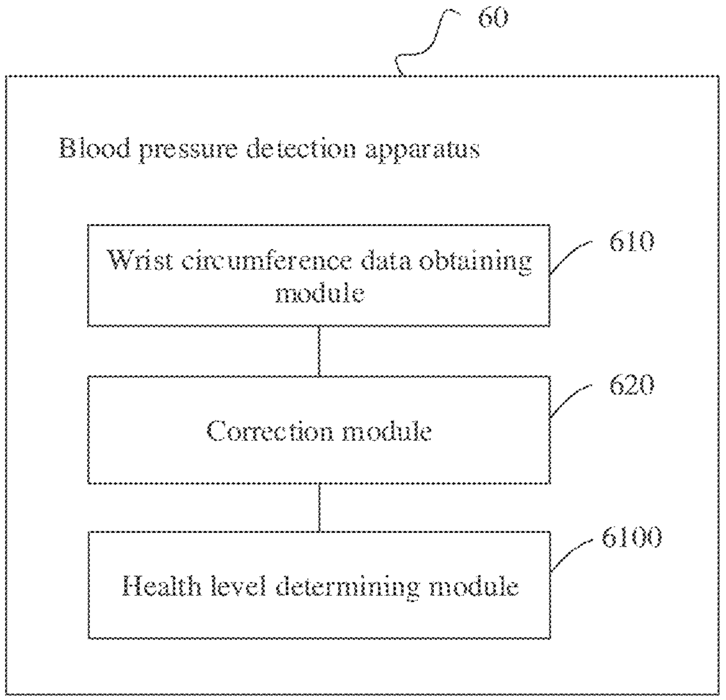
FIG. 21 is a schematic diagram of another structure of a blood pressure detection apparatus according to an embodiment of this application.

As shown in FIG. 21, the blood pressure detection apparatus 60 further includes a health level determining module 6100.

The health level determining module 6100 is configured to: determine a health level of a user based on the wrist fat thickness data and the detected blood pressure data; and display the health level.

Figure 22:
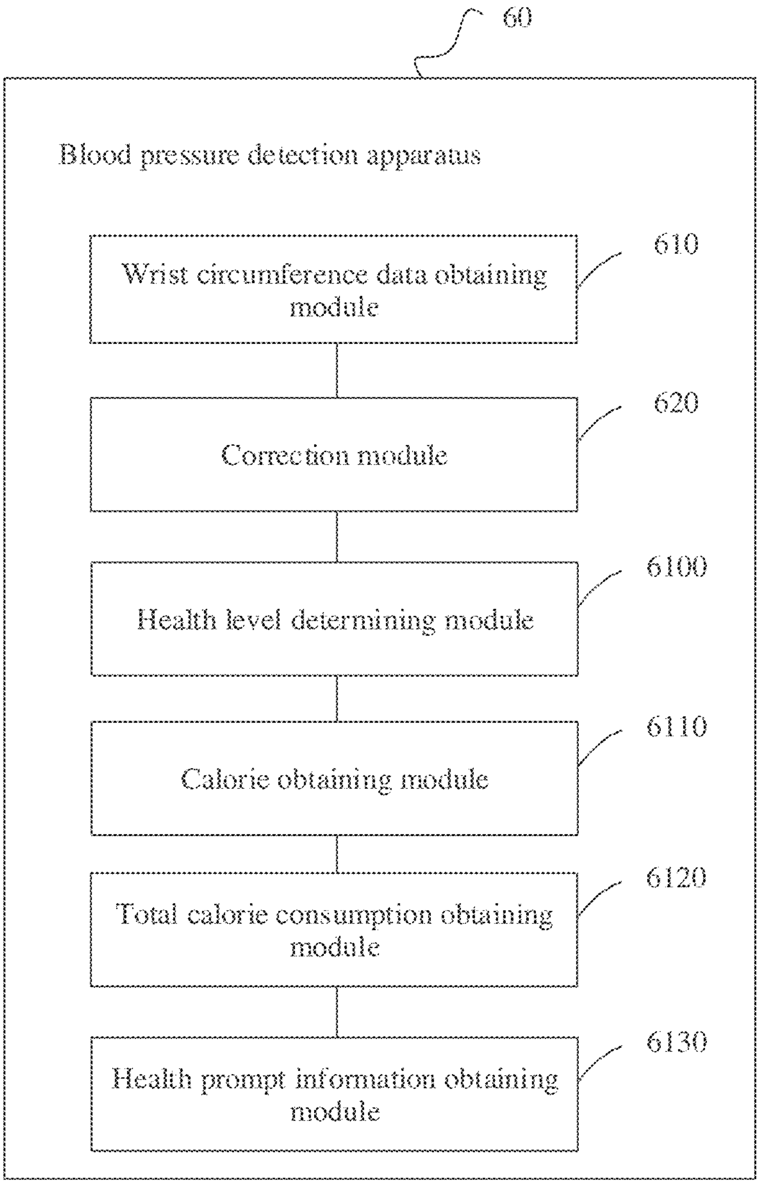
FIG. 22 is a schematic diagram of another structure of a blood pressure detection apparatus according to an embodiment of this application.

As shown in FIG. 22, the blood pressure detection apparatus 60 further includes a calorie obtaining module 6110, a total calorie consumption obtaining module 6120, and a health prompt information obtaining module 6130.

The calorie obtaining module 6110 is configured to obtain a total calorie intake of the user in unit time.

The total calorie consumption obtaining module 6120 is configured to obtain total calorie consumption of the user in the unit time.

The health prompt information obtaining module 6130 is configured to output health prompt information based on the total calorie intake, the total calorie consumption, and the health level.

The wrist circumference data obtaining module 610 includes an electrical parameter detection module 611_a_ and a wrist circumference data determining module 612_a_.

The electrical parameter detection module 611_a_ is configured to detect an electrical parameter of an adjustable component around a wrist of the user. The adjustable component includes at least one of an adjustable resistor, an adjustable capacitor, or an adjustable inductor.

The wrist circumference data determining module 612_a_ is configured to obtain wrist circumference data corresponding to the electrical parameter.

In an implementation, the wrist circumference data obtaining module 610 is further specifically configured to perform impedance detection on the wrist of the user to obtain the wrist fat thickness data. The wrist circumference data obtaining module 610 further includes:

a test current input module 611_b_, configured to input test currents on a plurality of frequencies to the user;

an electric potential difference detection module 612_b_, configured to detect a plurality of electric potential differences formed in a human body by the test currents on the plurality of frequencies; and a first wrist fat thickness data determining module 613_b_, configured to determine the wrist fat thickness data based on the plurality of test currents and the plurality of electric potential differences.

In another implementation, the wrist circumference data obtaining module 610 is further specifically configured to perform ultrasonic distance detection on the wrist of the user to obtain the wrist fat thickness data. The wrist circumference data obtaining module 610 further includes:

a first ultrasonic wave transmit module 611_c_, configured to: transmit a first ultrasonic wave to the wrist of the user, and record transmit time of the first ultrasonic wave;

a second ultrasonic wave capture module 612_c_, configured to: when the second ultrasonic wave is received, record receive time of the second ultrasonic wave, where the second ultrasonic wave is an ultrasonic wave reflected after the first ultrasonic wave reaches a bone of the wrist; and a second wrist fat thickness data determining module 613_c_, configured to determine the wrist fat thickness data based on the transmit time of the first ultrasonic wave and the receive time of the second ultrasonic wave.

As shown in FIG. 23, the correction module 620 includes a mapping relationship obtaining module 621 and a display module 622.

The mapping relationship obtaining module 621 is configured to: determine, based on the wrist circumference data and the wrist fat thickness data, that the blood pressure data needs to be corrected, and obtain, from a preset database, a mapping relationship corresponding to the wrist circumference data and the wrist fat thickness data.

The display module 622 is configured to: correct the blood pressure data based on the mapping relationship, and display the corrected blood pressure data.

Figure 24:
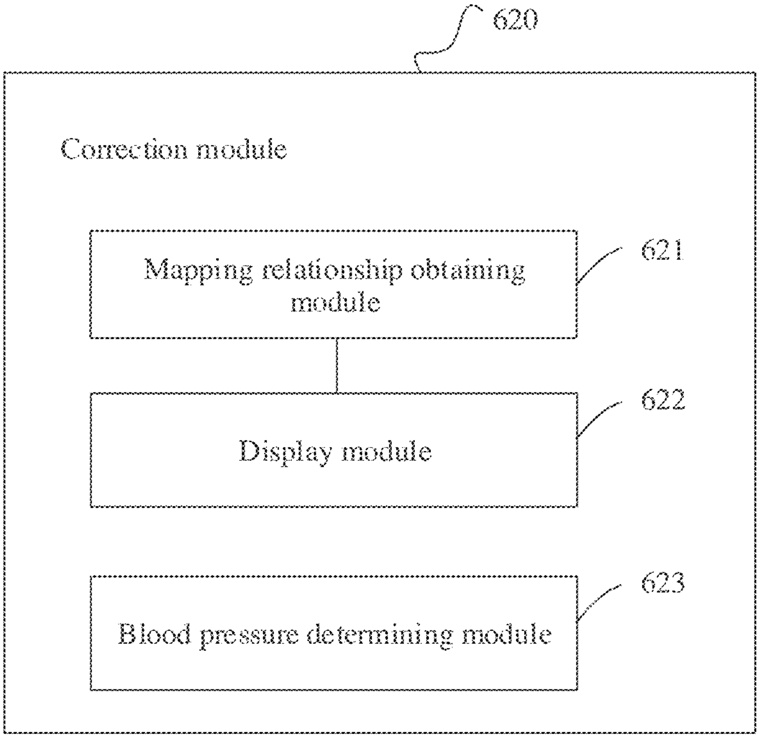
FIG. 24 is a schematic diagram of another structure of a correction module in a blood pressure detection apparatus according to an embodiment of this application.

As shown in FIG. 24, the correction module 620 further includes a blood pressure determining module 623.

The blood pressure determining module 623 is configured to: if the blood pressure data does not need to be corrected, display the blood pressure data.

Figure 25:
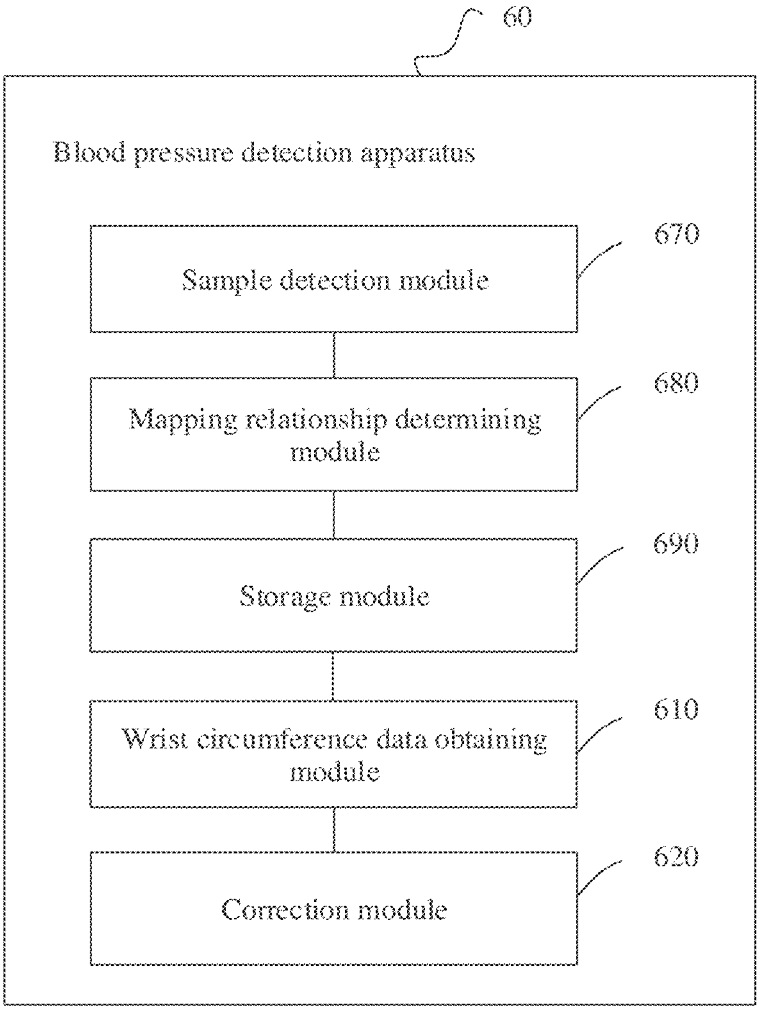
FIG. 25 is a schematic diagram of another structure of a blood pressure detection apparatus according to an embodiment of this application.

As shown in FIG. 25, the blood pressure detection apparatus 60 further includes a sample detection module 670, a mapping relationship determining module 680, and a storage module 690.

The sample detection module 670 is configured to obtain wrist circumference data, wrist fat thickness data, original blood pressure data, and standard blood pressure data of different figures of people.

The mapping relationship determining module 680 is configured to perform fitting on the wrist circumference data, the wrist fat thickness data, the original blood pressure data, and the standard blood pressure data of each figure of people to obtain a corresponding mapping relationship.

The storage module 690 is configured to store, in a database, the wrist circumference data, the wrist fat thickness data, and the corresponding mapping relationship of each figure of people.

It should be noted that content such as information exchange and an execution process between the apparatuses/units is based on the same idea as the method embodiments of this application. Therefore, for specific functions and beneficial effects, refer to the method embodiments. Details are not further described herein again.

It may be clearly understood by persons skilled in the art that, for the purpose of convenient and brief description, division of the foregoing function units and modules is used as an example for illustration. In actual application, the foregoing functions can be allocated to different function units and modules and implemented based on a requirement, that is, an inner structure of the apparatus is divided into different function units or modules to implement all or some of the functions described above. Function units and modules in embodiments may be integrated into one processing unit, or each of the units may exist alone physically, or two or more units are integrated into one unit. The integrated unit may be implemented through hardware, or may be implemented in a form of software function unit. In addition, specific names of the function units and modules are also used for ease of mutual distinction, and are not used to limit the protection scope of this application. For a detailed working process of the foregoing units and modules in the system, refer to a corresponding process in the foregoing method embodiments. Details are not described herein again.

An embodiment of this application further provides a computer-readable storage medium. The computer-readable storage medium stores a computer program. The computer program may be executed by a processor to implement steps in the method embodiments.

An embodiment of this application provides a computer program product. When the computer program product is run on a mobile electronic device, the electronic device is enabled to perform the steps in the method embodiments during execution.

When the integrated unit is implemented in a form of a software function unit and sold or used as an independent product, the integrated unit may be stored in a computer-readable storage medium. Based on such understanding, all or some of the processes of the methods in embodiments in this application may be implemented by a computer program instructing related hardware. The computer program may be stored in a computer-readable storage medium. When the computer program is executed by a processor, the steps of the method embodiments may be implemented. The computer program includes computer program code. The computer program code may be in a source code form, an object code form, an executable file, some intermediate forms, or the like. The computer-readable medium may include at least any entity or apparatus that can carry the computer program code in the electronic device, a recording medium, a computer memory, a read-only memory (ROM, Read-Only Memory), a random access memory (RAM, Random Access Memory), an electrical carrier signal, a telecommunications signal, and a software distribution medium, for example, a USB flash drive, a removable hard disk, a magnetic disk, or an optical disc. In some jurisdictions, according to legislation and patent practice, the computer-readable medium cannot be an electrical carrier signal or a telecommunications signal.

In the foregoing embodiments, the description of each embodiment has respective focuses. For a part that is not described in detail in an embodiment, refer to related descriptions in other embodiments.

Persons of ordinary skill in the art may be aware that, in combination with the examples described in embodiments disclosed in this specification, units and algorithm steps may be implemented by electronic hardware or a combination of computer software and electronic hardware. Whether the functions are performed by hardware or software depends on particular applications and design constraint conditions of the technical solutions. Persons skilled in the art may use different methods to implement the described functions for each particular application, but it should not be considered that the implementation goes beyond the scope of this application.

In embodiments provided in this application, it should be understood that the disclosed apparatus/network device and method may be implemented in other manners. For example, the described apparatus/network device embodiment is merely an example. For example, the division into modules and units is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of embodiments.

The foregoing embodiments are merely intended for describing the technical solutions of this application, but not for limiting this application. Although this application is described in detail with reference to the foregoing embodiments, persons of ordinary skill in the art should understand that they may still make modifications to the technical solutions described in the foregoing embodiments or make equivalent replacements to some technical features thereof, without departing from the spirit and scope of the technical solutions of embodiments of this application, and these modifications and replacements shall fall within the protection scope of this application.

What is claimed is:

1. A method, comprising:

obtaining, by a wearable device, wrist circumference data, wrist fat thickness data, and blood pressure data of a user wearing the wearable device, wherein obtaining the wrist circumference data comprises:

detecting an electrical parameter of an adjustable component around a wrist of the user, wherein the adjustable component comprises at least one of an adjustable resistor, an adjustable capacitor, or an adjustable inductor; and determining the wrist circumference data based on the electrical parameter;

determining, based on the wrist circumference data, at least one wrist circumference threshold, the wrist fat thickness data, and at least one wrist fat thickness threshold, whether the blood pressure data needs to be corrected, comprising:

when the wrist fat thickness data is less than a first wrist fat thickness threshold, and the wrist circumference data is less than a second wrist circumference threshold, determining that the blood pressure data does not need to be corrected;

when the wrist fat thickness data is less than the first wrist fat thickness threshold, and the wrist circumference data is greater than the second wrist circumference threshold, determining that the blood pressure data needs to be corrected; and when the wrist fat thickness data is less than a second wrist fat thickness threshold and greater than the first wrist fat thickness threshold, and the wrist circumference data is greater than a first wrist circumference threshold and less than the second wrist circumference threshold, determining that the blood pressure data needs to be corrected; and when it is determined that the blood pressure data needs to be corrected, correcting, by the wearable device, the blood pressure data based on both the wrist circumference data and the wrist fat thickness data.

2. The method according to claim 1, wherein obtaining the wrist fat thickness data comprises:

performing impedance detection on a wrist of the user to obtain the wrist fat thickness data; or performing ultrasonic distance detection on a wrist of the user to obtain the wrist fat thickness data.

3. The method according to claim 2, wherein performing impedance detection on the wrist of the user to obtain the wrist fat thickness data comprises:

inputting test currents associated with a plurality of frequencies to the wrist of the user, wherein each of the test currents is at a respective frequency of the plurality of frequencies;

detecting a plurality of electric potential differences formed at the wrist by the test currents; and determining the wrist fat thickness data based on the test currents and the plurality of electric potential differences.

4. The method according to claim 2, wherein performing ultrasonic distance detection on the wrist of the user to obtain the wrist fat thickness data comprises:

transmitting a first ultrasonic wave to the wrist of the user, and recording transmit time of the first ultrasonic wave;

when receiving a second ultrasonic wave, recording receive time of the second ultrasonic wave, wherein the second ultrasonic wave is an ultrasonic wave reflected after the first ultrasonic wave reaches a bone of the wrist; and determining the wrist fat thickness data based on the transmit time of the first ultrasonic wave and the receive time of the second ultrasonic wave.

5. The method according to claim 1, wherein before obtaining the wrist circumference data, the method further comprises:

obtaining sets of reference wrist circumference data, reference wrist fat thickness data, reference original blood pressure data, and reference blood pressure data, wherein the sets of reference wrist circumference data, reference wrist fat thickness data, reference original blood pressure data, and reference blood pressure data comprise data from people of different body types;

performing fitting on the sets of reference wrist circumference data, reference wrist fat thickness data, reference original blood pressure data, and reference blood pressure data of each body type of the different body types, to obtain a corresponding mapping relationship; and storing, in a database, the reference wrist circumference data, the reference wrist fat thickness data, and a corresponding mapping relationship of each body type of people.

6. The method according to claim 1, wherein after correcting, by the wearable device, the blood pressure data based on the wrist circumference data and the wrist fat thickness data, the method further comprises:

determining, by the wearable device, a health level of the user based on the wrist fat thickness data and the detected blood pressure data; and displaying, by the wearable device, the health level.

7. The method according to claim 6, wherein after determining the health level of the user, the method further comprises:

obtaining, by the wearable device, a total calorie intake of the user within a unit of time;

obtaining, by the wearable device, total calorie consumption of the user within the unit of time; and outputting, by the wearable device, health prompt information based on the total calorie intake, the total calorie consumption, and the health level.

8. The method according to claim 1, wherein correcting, by the wearable device, the blood pressure data based on the wrist circumference data and the wrist fat thickness data comprises:

when determining, based on the wrist circumference data and the wrist fat thickness data, that the blood pressure data needs to be corrected, obtaining, by the wearable device from a preset database, a mapping relationship corresponding to the wrist circumference data and the wrist fat thickness data; and correcting, by the wearable device, the blood pressure data based on the mapping relationship, and displaying corrected blood pressure data.

9. The method according to claim 1, wherein determining, based on the wrist circumference data, at least one wrist circumference threshold, the wrist fat thickness data, and at least one wrist fat thickness threshold, whether the blood pressure data of the user corresponding to the wearable device needs to be corrected, further comprises:

when the wrist fat thickness data is greater than the first preset wrist fat thickness threshold, and the wrist circumference data is less than the first wrist circumference threshold, determining that the blood pressure data does not need to be corrected; and when the wrist fat thickness data is less than the second wrist fat thickness threshold and greater than the first wrist fat thickness threshold, and the wrist circumference data is greater than the second wrist circumference threshold, determining that the blood pressure data needs to be corrected.

10. An electronic device, comprising:

a main body;

one or more processors;

one or more memories, wherein the one or more processors and the one or more memories are disposed in the main body, wherein one or more computer programs are stored in the one or more memories, the one or more computer programs comprise instructions, and when the instructions are executed by the electronic device, the electronic device is enabled to perform:

obtaining wrist circumference data, wrist fat thickness data, and blood pressure data of a user wearing the electronic device, wherein obtaining the wrist circumference data comprises:

detecting an electrical parameter of an adjustable component around a wrist of the user, wherein the adjustable component comprises at least one of an adjustable resistor, an adjustable capacitor, or an adjustable inductor; and determining the wrist circumference data based on the electrical parameter;

determining, based on the wrist circumference data, at least one wrist circumference threshold, the wrist fat thickness data, and at least one wrist fat thickness threshold, whether the blood pressure data needs to be corrected, comprising:

when the wrist fat thickness data is less than a first wrist fat thickness threshold, and the wrist circumference data is less than a second wrist circumference threshold, determining that the blood pressure data does not need to be corrected;

when the wrist fat thickness data is less than the first wrist fat thickness threshold, and the wrist circumference data is greater than the second wrist circumference threshold, determining that the blood pressure data needs to be corrected; and when the wrist fat thickness data is less than a second wrist fat thickness threshold and greater than the first wrist fat thickness threshold, and the wrist circumference data is greater than a first wrist circumference threshold and less than the second wrist circumference threshold, determining that the blood pressure data needs to be corrected; and when it is determined that the blood pressure data needs to be corrected, correcting the blood pressure data based on both the wrist circumference data and the wrist fat thickness data.

11. The electronic device according to claim 10, wherein when the instructions are executed by the electronic device, the electronic device is further enabled to perform:

inputting test currents associated with a plurality of frequencies to the wrist of the user, wherein each of the test currents is at a respective frequency of the plurality of frequencies;

detecting a plurality of electric potential differences formed at the wrist by the test currents; and determining the wrist fat thickness data based on the est currents and the plurality of electric potential differences.

12. The electronic device according to claim 10, wherein when the instructions are executed by the electronic device, the electronic device is further enabled to perform:

determining a health level of the user based on the wrist fat thickness data and the blood pressure data or the corrected blood pressure data; and displaying the health level.

13. The electronic device according to claim 12, wherein when the instructions are executed by the electronic device, the electronic device is further enabled to perform:

obtaining calorie intake information, wherein the calorie intake information indicates a total calorie intake of the user during a unit time period;

obtaining calorie consumption information, wherein the calorie consumption information indicates total calorie consumption of the user during the unit time period; and outputting health prompt information based on the total calorie intake, the total calorie consumption, and the health level.

14. The electronic device according to claim 10, wherein when the instructions are executed by the electronic device, the electronic device is further enabled to perform:

when determining, based on the wrist circumference data and the wrist fat thickness data, that the blood pressure data needs to be corrected, obtaining, from a preset database, a mapping relationship corresponding to the wrist circumference data and the wrist fat thickness data; and correcting the blood pressure data based on the mapping relationship, and displaying corrected blood pressure data.

15. The electronic device according to claim 10, further comprising:

a strap connected to the main body, wherein the strap is configured to enable the user to wear the main body on a wrist of the user;

wherein the strap comprises a first strap and a second strap, and the first strap and the second strap are separately connected to the main body;

wherein the adjustable component is disposed on a first surface of the first strap, and the first surface is a surface facing the wrist when the electronic device is worn on the wrist of the user;

wherein a plurality of holes extend in the first strap and are parallel to the adjustable component, and the adjustable component is connected to the plurality of holes through a first conducting wire; and wherein the second strap comprises a buckle tongue matching the plurality of holes, a second conducting wire is disposed on both surfaces of the buckle tongue and the plurality of holes, and when the buckle tongue is connected to the holes through the second conducting wire, the electrical parameter of the adjustable component may be adjusted based on a position of the buckle tongue.

16. The electronic device according to claim 10, further comprising:

a strap comprising a first strap and a second strap connected to the main body, wherein the first strap and the second strap are configured to allow the user to wear the main body on a wrist of the user;

wherein the adjustable component is disposed on a first surface of the first strap, the first surface faces the wrist when the electronic device is worn on the wrist of the user, an insulator is disposed on a surface of the adjustable component, and a plurality of third conducting wires are embedded in the insulator in a spaced manner and connected to the adjustable component; and wherein the second strap comprises a movable butterfly clasp, the butterfly clasp is connected to the adjustable component through the third conducting wires, and when the butterfly clasp moves on the strap, the electrical parameter of the adjustable component may be adjusted based on a position of the butterfly clasp.

17. The electronic device according to claim 10, further comprising:

an excitation electrode, a detection electrode, and an impedance detection circuit;

wherein the excitation electrode is disposed on a side surface of the main body and is configured to forward an excitation voltage;

wherein the detection electrode is disposed at a bottom of the main body and is configured to receive a detection voltage, wherein the detection voltage is generated based on the excitation voltage and a voltage drop of wrist fat of the user; and wherein the impedance detection circuit is disposed in the main body and is configured to: generate the excitation voltage, and obtain the wrist fat thickness data through calculation based on the excitation voltage and the detection voltage.

18. The electronic device according to claim 10, further comprising:

a plurality of excitation electrodes, wherein the excitation electrodes are sequentially arranged on a side surface of the main body; and a plurality of detection electrodes, wherein the detection electrodes are disposed at a bottom of the main body and are sequentially arranged along a periphery of the bottom of the main body, and wherein each excitation electrode is connected to one detection electrode.

19. The electronic device according to claim 10, further comprising:

an air pump, an airbag, and a pressure sensor;

wherein the air pump and the pressure sensor are disposed in the main body, the airbag is disposed on a second surface of a strap, and the second surface is a contact surface of the strap with a wrist of the user when the electronic device is worn on the wrist of the user;

wherein the air pump is connected to the airbag, and the airbag is connected to the pressure sensor;

wherein the air pump is configured to inflate the airbag; and wherein the pressure sensor is configured to: in a process of inflating the airbag, detect air pressure in the airbag in real time, and obtain the blood pressure data through calculation based on the air pressure.

20. The electronic device according to claim 10, wherein determining, based on the wrist circumference data, at least one wrist circumference threshold, the wrist fat thickness data, and at least one wrist fat thickness threshold, whether the blood pressure data needs to be corrected, further comprises:

when the wrist fat thickness data is greater than the first wrist fat thickness threshold, and the wrist circumference data is less than the first wrist circumference threshold, determining that the blood pressure data does not need to be corrected; and when the wrist fat thickness data is less than the second wrist fat thickness threshold and greater than the first wrist fat thickness threshold, and the wrist circumference data is greater than the second wrist circumference threshold, determining that the blood pressure data needs to be corrected.

* * * * *